US009150531B2

(12) United States Patent
Gidlöf et al.

(10) Patent No.: US 9,150,531 B2
(45) Date of Patent: Oct. 6, 2015

(54) TRICYCLIC LACTONES FOR TREATMENT OF CANCER

(75) Inventors: Ritha Gidlöf, Lund (SE); Martin Johansson, Heberg (SE); Olov Sterner, Malmö (SE); Eduardo Muñoz, Cordova (ES)

(73) Assignee: Glactone Pharma Development AB, Helsingborg (SE)

( * ) Notice: Subject to any disclaimer, the term of this patent is extended or adjusted under 35 U.S.C. 154(b) by 0 days.

(21) Appl. No.: 13/811,015

(22) PCT Filed: Jul. 18, 2011

(86) PCT No.: PCT/EP2011/062243
§ 371 (c)(1),
(2), (4) Date: Aug. 5, 2013

(87) PCT Pub. No.: WO2012/010555
PCT Pub. Date: Jan. 26, 2012

(65) Prior Publication Data
US 2013/0310451 A1    Nov. 21, 2013

(30) Foreign Application Priority Data
Jul. 19, 2010   (SE) ..................................... 1050815

(51) Int. Cl.
| C07D 303/40 | (2006.01) |
| C07D 307/93 | (2006.01) |
| C07D 303/38 | (2006.01) |
| A61K 31/336 | (2006.01) |
| A61K 31/365 | (2006.01) |
| A61K 45/06  | (2006.01) |

(52) U.S. Cl.
CPC ............ *C07D 307/93* (2013.01); *A61K 31/336* (2013.01); *A61K 31/365* (2013.01); *A61K 45/06* (2013.01); *C07D 303/38* (2013.01); *C07D 303/40* (2013.01)

(58) Field of Classification Search
CPC .................................................... C07D 303/40
See application file for complete search history.

(56) References Cited

U.S. PATENT DOCUMENTS 6,512,007 B1   1/2003   Baumgarten et al.

FOREIGN PATENT DOCUMENTS

| WO | WO-02/02109 A1 | 1/2002 |
| WO | WO-2008/135419 A2 | 11/2008 |

OTHER PUBLICATIONS

Sterner, O., et al. "Tandem Pd-atalyzed Carbonylation and Intramolecular Vinyl Allene Diels-Alder Reaction Toward Galiellalactone." Organic Letters. (2010), vol. 12, No. 22, pp. 5100-5103.*
American Cancer Society (ACS). © 2013. Available from: < http://www.cancer.org/cancer/showallcancertypes/index >.*
Navigating Cancer, Inc. "List of List of Cancer Chemotherapy Drugs." © 2013. Available from: < https://www.navigatingcancer.com/library/all/chemotherapy_drugs >.*
Baade, P. "One in four cancers preventable—but first we need the willpower." © 2012. Available from: < http://theconversation.com/one-in-four-cancers-preventable-but-first-we-need-the-willpower-5850 >.*
Santer, F., et al. "Interleukin-6 trans-signaling differentially regulates proliferation, migration, adhesion, and maspin expression in human prostate cancer cells." Endocrine-Related Cancer (2010), vol. 17, pp. 241-253.*
Decker, T., et al. "Constitutively activated phosphatidylinositol-3 kinase (PI3K) is involved in the defect of apoptosis in B-CLL: association with protein kinase C-δ." Blood. (Nov. 15, 2002), vol. 100, No. 10, pp. 3741-3748.*
Mayo Clinic. "Prostate cancer prevention: What you can do." © Dec. 6, 2008. Available from: < http://web.archive.org/web/20081206101911/http://www.mayoclinic.com/health/prostate-cancer-prevention/MC00027 >.*
Mayo Clinic. "Pancreatic cancer." (C) 2013. Available from: < http://www.mayoclinic.com/health/pancreatic-cancer/DS00357/METHOD=print >.*
Mayo Clinic. "Alzheimer's Disease." © 2013. Available from: < http://www.mayoclinic.com/health/alzheimers-disease/DS00161/METHOD=print&DSECTION=all >.*
Mayo Clinic. "Parkinson's Disease." © 2013. Available from: < http://www.mayoclinic.com/health/parkinsons-disease/DS00295/METHOD=print&DSECTION=all >.*
International Search Report in International Application No. PCT/EP2011/062243, filed Jul. 18, 2011.
Nussbaum, F. V. et al. "The High-Intrinsic Diels—Alder Reactivity of (-)-Galiellalactone; Generating Four Quaternary Carbon Centers under Mild Conditions" *European Journal of Organic Chemistry*, Jul. 2004, 13:2783-2790.
Köpcke, B. et al. "Galiellalactone and its biogenetic precursors as chemotaxonomic markers of the Sarcosomataceae (Ascomycota)" *Phytochemistry*, Aug. 2002, 60(7):709-714.
Weidler, M. et al. "Inhibition of interleukin-6 signaling by galiellalactone" *FEBS Letters*, Oct. 27, 2000, 484(1):1-6.
Gidlöf, R. et al. "Tandem Pd-Catalyzed Carbonylation and Intramolecular Vinyl Allene Diels—Alder Reaction toward Galiellalactone Analogues" *Organic Letters*, Nov. 19, 2010, 12(22):5100-5103.
Johansson, M. et al. "Synthesis of (-)-Galiellalactone" *The Journal of Antibiotics*, Jul. 2002, 55(7):663-665.

(Continued)

*Primary Examiner* — Andrew D Kosar
*Assistant Examiner* — John S Kenyon
(74) *Attorney, Agent, or Firm* — Saliwanchik, Lloyd & Eisenschenk

(57) ABSTRACT

The present invention discloses novel compounds useful for the inhibition of IL-6/STAT signaling and/or PI3K/NF-κB signaling in the treatment of associated diseases or conditions, e.g. cancer. A pharmaceutical composition comprising such novel compounds, its use and a method thereof, is also disclosed.

17 Claims, No Drawings

(56) References Cited

OTHER PUBLICATIONS

Appendino, G. et al. "Arzanol, an Anti-inflammatory and Anti-HIV-1 Phloroglucinol α-Pyrone from *Helichrysum italicum ssp. microphyllum*" *Journal of Natural Products*, Apr. 2007, 70(4):608-612.

Appendino, G. et al. "A Meroterpenoid NF-κB Inhibitor and Drimane Sesquiterpenoids from Asafetida" *Journal of Natural Products*, Jul. 2006, 69(7):1101-1104.

Márquez, N. et al. "Mesuol, a natural occurring 4-phenylcoumarin, inhibits HIV-1 replication by targeting the NF-κB pathway" *Antiviral Research*, Jun. 2005, 66(2-3):137-145.

Mandai, T. et al. "Palladium-catalyzed Tandem Carbonylation and Intramolecular Diels-Alder Reaction of 4-alken-2-ynyl Carbonates: A New Synthetic Method for Polycyclic Compounds" *Tetrahedron Letters*, Dec. 23, 1991, 32(52):7687-7688.

Hellsten, R. et al. "Galiellalactone is a Novel Therapeutic Candidate Against Hormone-Refractory Prostate Cancer Expressing Activated Stat3" *The Prostate*, Feb. 15, 2008, 68(3):269-280.

Johansson, M. et al. "Synthesis of (+)-Galiellalactone. Absolute Configuration of Galiellalactone" *Organic Letters*, Sep. 6, 2001, 3(18):2843-2845.

Lemiére, G. et al. "Tandem Gold(I)-Catalyzed Cyclization/Electrophilic Cyclopropanation of Vinyl Allenes" *Organic Letters*, May 24, 2007, 9(11):2207-2209.

\* cited by examiner

TRICYCLIC LACTONES FOR TREATMENT OF CANCER

CROSS-REFERENCE TO RELATED APPLICATIONS

This application is the U.S. national stage application of International Patent Application No. PCT/EP2011/062243, filed Jul. 18, 2011, which claims priority to Swedish Application No. 1050815-8, filed Jul. 19, 2010, the disclosures of each of which are incorporated herein by reference in their entirety.

TECHNICAL FIELD

The present invention relates to novel tricyclic compounds, pharmaceutical compositions comprising such compounds, and a method of treating or alleviating conditions, in particular cancer, by use of such compounds.

BACKGROUND

IL-6 is a pleiotropic cytokine with a wide range of biological activities in the fields of immune regulation, hematopoiesis, inflammation and oncogenesis. It is produced by numerous cell types and acts on a large and diverse population of cells and tissues. Binding of IL-6 to the IL-6 receptor leads to the recruitment and complex formation of two gp130 molecules at the cell membrane. The intracellular dimerization of two gp130 proteins recruits members of the Janus family of tyrosine kinases (JAKs) to the complex, allowing trans-phosphorylation. JAKs subsequently phosphorylate additional targets, including the gp130 receptor, whose phosphorylation is necessary for the phosphorylation and activation of the signal transducers and activators of transcription (STAT), mainly STAT3 and STAT1. Activation of STATs leads to the formation of stable STAT complexes due to either homo- or heterodimerization. The phosphorylation and dimerization of the STAT-protein also exposes its nuclear localization signal, leading to translocation of the complex to the nucleus for binding to the promoter region of target genes, including cyclin D, c-myc, p21, p2'7, Bcl-2 and VEGF.

In a healthy organism, IL-6 is expressed at low levels controlled by a complex network comprising e.g. glucocorticoids and catecholamines. However, accumulating evidence indicates pathological roles for IL-6 in various disease conditions, including autoimmune, inflammatory and malignant diseases. These conditions are coupled to enhanced activation of the IL-6 signaling pathway, and the unchecked production from the IL-6 target genes may arise due to mutations in one or several different steps/proteins in the pathway. Normally the STAT3 activation is tightly regulated and activated STAT3 proteins are dephosphorylated by phosphatases and transported out of the nucleus. Aberrant and deregulated STAT3 promotes cell proliferation and cell survival in both solid and hematological tumors, including breast, lung, brain, colon, prostate, lymphoma and leukemia.

Also, the IL-6 signaling pathway is coupled to the Ras/MAPK- and PI3K signaling pathways. These are the major signaling patways regulating e.g. proliferation, survival and differentiation of cells, and they are frequently mutated in a variety of human diseases, including cancer and inflammatory diseases. For instance, aberrant regulation of the transcription factor NF-κB in the PI3K-pathway is associated with cancer development and progression, as well as in resistance to chemotherapy. Further, there is significant interactions (cross talk) between NF-κB and STAT3, including overlapping genes, co-transcription and co-localization, and thereby, NF-κB and STAT3 cooperate to promote development of several cancers.

(−)-Galiellalactone is a natural product isolated from wood-inhabiting fungi with submicromolar inhibition of IL-6/STAT3 signaling.

Nussbaum et al reports in Eur. J. Org. Chem. 2004, 2783-2790 on the modification of individual functional groups of (−)-galiellalactone. Most of the resulting analogues, however, turned out to be inactive or less active than (−)-galiellalactone.

Weidler et al reports in FEBS Letters 2000, 484, 1-6 that the biological effect of (−)-galiellalactone seemingly is due to a direct inhibition of the binding of STAT3-dimers to their regulatory elements.

U.S. Pat. No. 6,512,007 describe the use of galiella lactone as a pharmaceutical for the treatment of e.g. inflammatory processes.

The treatments for prevention, revocation or reduction of deceases like e.g. cancer are in many ways insufficient. Hence, compounds effective in modulating or inhibiting the above described IL-6/STAT signaling and/or PI3K/NF-κB signaling are desired.

SUMMARY

The present invention seeks to mitigate, alleviate, circumvent or eliminate at least one, such as one or more, of the above-identified deficiencies.

Accordingly there is provided, according to one aspect of the invention, a compound, which may be represented by the general formulas (I) or (II)

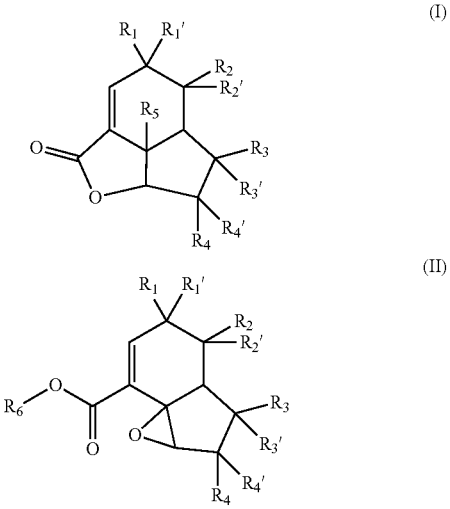

wherein $R_1$ and $R_1'$ are independently selected from the group consisting of H, C1-5alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl) SO2C1-5 fluoroalkyl; $R_2$ and $R_2'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl) SO2C1-5 fluoroalkyl; $R_3$ and $R_3'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl) SO2C1-5 fluoroalkyl; $R_4$ and $R_4'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl) SO2C1-5 fluoroalkyl; $R_5$ is selected from the group consisting of OC0-5 alkyl, OC1-5 fluoroalkyl, OC(O)C1-5 alkyl, OC2-3 alkyleneN(C0-5 alkyl)2 in which the C0-5 alkyl may be the same or different, NHC0-5 alkyl, N(C1-5 alkyl)2 in which the C1-5 alkyl may be the same or different, N(C0-5 alkyl)C(O)C1-5 alkyl, NHaryl, NHheteroaryl, a 3- to 8-membered non-aromatic heterocycle which is connected via a substitutable heteroatom of said non-aromatic heterocycle, SC0-5 alkyl, S(O)C0-5 alkyl, SO2C0-5 alkyl, and N(C0-C3 alkyl)SO2C1-C5 alkyl; $R_6$ is selected from the group consisting of H, C1-5 alkyl, C1-5 fluoroalkyl, and a C3-8 non-aromatic carbocycle; and at least one of $R_2, R_2', R_3, R_3', R_4$ and $R_4'$ is comprising a carbon atom, an oxygen atom or a nitrogen atom; as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

According to another aspect, there is provided a compound of formula (I), wherein the relative or absolute stereochemistry of $R_1, R_1', R_2, R_2', R_3, R_3', R_4, R_4', R_5$ and the hydrogen atoms at positions 5a and 7a of the compound of formula (I) is

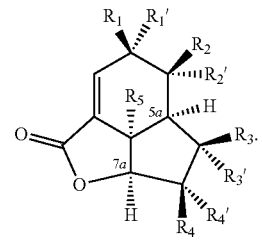

According to yet another aspect, there is provided a compound of formula (II), wherein the relative or absolute stereochemistry of $R_1, R_1', R_2, R_2', R_3, R_3', R_4, R_4'$, the hydrogen atom at positions 5a and the oxygen atom at position 7a and 7b of the compound of formula (II) is

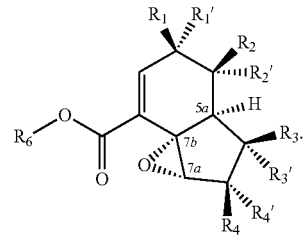

According to yet another aspect, at least one of $R_1, R_1', R_2, R_2', R_3, R_3', R_4$ and $R_4'$ may be selected from the group consisting of H, d 1-5 alkyl, aryl, CH2aryl, heteroaryl and CH2heteroaryl.

According to yet another aspect, at least one of $R_2, R_2', R_3, R_3', R_4$ and $R_4'$ may be selected from the group consisting of H, C1-5 alkyl, aryl, CH2aryl, heteroaryl and CH2heteroaryl.

According to yet another aspect, at least one of $R_2, R_2', R_3, R_3', R_4$ and $R_4'$ may be selected from the group consisting of C1-5 alkyl, aryl, CH2aryl, heteroaryl and CH2heteroaryl.

According to yet another aspect, at least one of $R_3, R_3', R_4$ and $R_4'$ may be selected from the group consisting of C1-5 alkyl, aryl, CH2aryl, heteroaryl and CH2heteroaryl.

According to yet another aspect, at least one of $R_4$ and $R_4'$ may be selected from the group consisting of C1-5 alkyl, aryl, CH2aryl, heteroaryl and CH2heteroaryl.

According to yet another aspect, one or both of $R_4$ and $R_4'$ may be H.

According to yet another aspect, both of $R_1$ and $R_1'$ may be H, or one of $R_1$ and $R_1'$ may be H and the other one of $R_1$ and $R_1'$ may be methyl.

According to yet another aspect, $R_6$ may be C1-5 alkyl and $R_5$ may be OH, OC1-5, OC1-5 fluoroalkyl, or OC(O)C1-5 alkyl.

According to yet another aspect, $R_1$, $R_1'$, $R_2$, $R_2'$ $R_3$, $R_3'$, $R_4$ and $R_4'$ may be independently selected from the group consisting of H, C1-5 alkyl, aryl, CH2aryl, heteroaryl and CH2heteroaryl; $R_5$ may be OH, NHC0-5 alkyl, NHaryl or NHheteroaryl; and $R_6$ may be C1-5 alkyl.

According to yet another aspect, the compound of formula (I) or (II) may be selected from the group consisting of

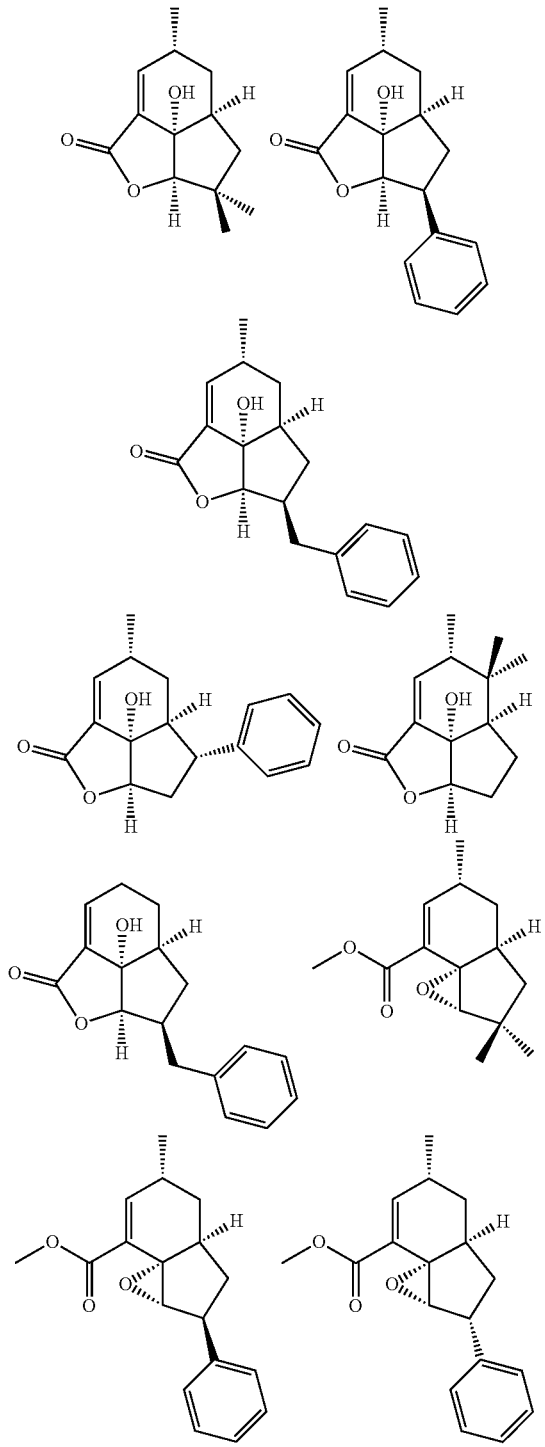

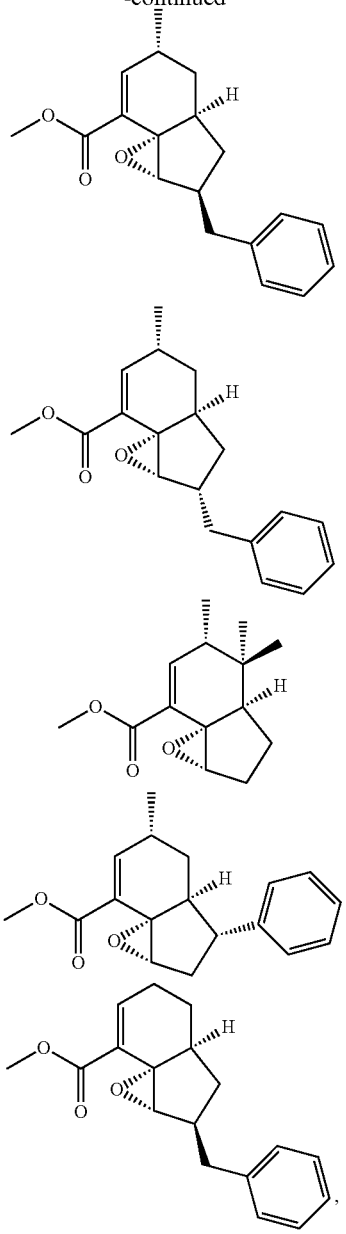

wherein the indicated stereochemistry is relative stereochemistry.

According to yet another aspect of the invention, the compound of formula (I) or (II) may be in a crystalline form.

According to yet another aspect of the invention, there is provided a pharmaceutical composition, which may comprise a compound of formula (I) or (II) and at least one pharmaceutically acceptable carrier or excipient.

According to yet another aspect of the invention, there is provided a pharmaceutical composition, which may comprise compound of formula (I) or (II) and at least one more therapeutic agent.

According to yet another aspect of the invention, the at least one more therapeutic agent may be selected from the group consisting of Abraxane, Aldesleukin, Alemtuzumab, Aminolevulinic Acid, Anastrozole, Aprepitant, Arsenic Trioxide, Azacitidine, Bendamustine Hydrochloride, Bevacizumab, Bexarotene, Bortezomib, Bleomycin, Cabazitaxel, Capecitabine, Carboplatin, Cetuximab, Cisplatin, Clofarabine, Cyclophosphamide, Cytarabine, Dacarbazine, Dasatinib, Daunorubicin Hydrochloride, Decitabine, Degarelix, Denileukin Diftitox, Dexrazoxane Hydrochloride, Docetaxel, Doxorubicin Hydrochloride, Doxorubicin Hydrochloride Liposome, Eltrombopag Olamine, Epirubicin Hydrochloride, Erlotinib Hydrochloride, Etoposide, Etoposide Phosphate, Everolimus, Exemestane, Filgrastim, Fludarabine Phosphate, Fluorouracil, Fulvestrant, Gefitinib, Gemcitabine Hydrochloride, Ibritumomab Tiuxetan, Imatinib Mesylate, Imiquimod, Irinotecan Hydrochloride, Ixabepilone, Lapatinib Ditosylate, Lenalidomide, Letrozole, Leucovorin Calcium, Leuprolide Acetate, Liposomal Cytarabine, Methotrexate, Nelarabine, Nilotinib, Ofatumumab, Oxaliplatin, Paclitaxel, Palifermin, Palonosetron Hydrochloride, Panitumumab, Pazopanib Hydrochloride, Pegaspargase, Pemetrexed Disodium, Plerixafor, Pralatrexate, Raloxifene Hydrochloride, Rasburicase, Recombinant HPV Bivalent Vaccine, Recombinant HPV Quadrivalent Vaccine, Rituximab, Romidepsin, Romiplostim, Sipuleucel-T, Sorafenib Tosylate, Sunitinib Malate, Talc, Tamoxifen Citrate, Temozolomide, Temsirolimus, Thalidomide, Topotecan Hydrochloride, Toremifene, Tositumomab and I 131 Iodine Tositumomab, Trastuzumab, Vincristine Sulfate, Vorinostat and Zoledronic Acid.

According to yet another aspect of the invention, a compound of formula (I) or (II), or pharmaceutical composition comprising either of these, may be used in therapy.

According to yet another aspect of the invention, a compound of formula (I) or (II), or pharmaceutical composition comprising either of these, may be used for the manufacture of a medicament for the treatment of an IL-6/STAT signaling related disorder or an PI3K/NF-κB signaling related disorder.

According to yet another aspect of the invention, the disorder may be solid cancer, hematological cancer, benign tumor, hyperproliferative disease, inflammation, autoimmune disease, graft or transplant rejection, delayed physiological function of grafts or transplants, neurodegenerative disease or viral infection.

According to yet another aspect of the invention, the disorder may be sarcoma, breast cancer, prostate cancer, head and neck cancer, brain tumor, colorectal cancer, lung cancer, pancreatic cancer, cervical cancer, ovarian cancer, melanoma, gastric cancer, renal cell carcinoma, endometrial cancer, sarcoma, hepatocellular carcinoma, chronic myelogenous leukemia, acute myelogenous leukemia, cutaneous T-cell lymphoma, Hodgkin's disease, anaplastic large-cell lymphoma, Burkitt's lymphoma, Cardiac myxoma, Castleman's disease, atherosclerosis, diabetes type 2, dementia, osteoporosis, hypertension, coronary artery disease, arthritis, Crohn's disease, ulcerative colitis, rheumatoid arthritis, inflammatory bowel disease, asthma, allergy, atopic dermatitis, systemic lupus erythematosus, uveitis, COPD, Parkinson's disease, Alzheimer's disease, multiple sclerosis, stroke and ischemia reperfusion injury, hepatitis C, herpes, infections caused by Kaposis Sarcoma-associated herpes virus (KSHV), Epstein-Barr virus related infections or psoriasis.

According to yet another aspect of the invention, a method for the treatment or prevention of an IL-6/STAT signaling related disorder or an PI3K/NF-κB signaling related disorder, wherein an effective amount of a compound of formula (I) or (II), or an effective amount of a pharmaceutical composition comprising a compound of formula (I) or (II), is administered to a subject in need of such treatment or prevention, is provided.

Further, advantageous features of various embodiments of the invention are defined in the dependent claims and within the detailed description below.

DETAILED DESCRIPTION

Definitions

In the context of the present application and invention, the following definitions apply:

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(C0 alkyl)2" is equivalent to "NH2" (amino).

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" or "C1-6 alkylene" denotes alkylenyl or alkylene having 1, 2, 3, 4, 5 or 6 carbon atoms. When the specific number denoting the alkylenyl or alkylene-group is the integer 0 (zero), a bond is intended to link the groups onto which the alkylenyl or alkylene-group is substituted. For example, "NH(C0 alkylene)NH2" is equivalent to "NHNH2" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "H2N(C2 alkylene)NH2", "H2N(C3 alkylene) NH2", "N(C4 alkylene)", "N(C5 alkylene)" and "N(C2 alkylene)2NH" is equivalent to 1,2-diamino ethane, 1,3-diamino propane, pyrrolidinyl, piperidinyl and piperazinyl, respectively.

Examples of alkyl include, but are not limited to, methyl, ethyl, n-propyl, propyl, n-butyl, i-butyl, sec-butyl, t-butyl, pentyl, and hexyl.

Examples of alkylene or alkylenyl include, but are not limited to, methylene, ethylene, propylene, and butylene.

As used herein, "alkoxy" or "alkyloxy" is intended to mean an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to any of the carbons of the corresponding alkyl, alkylene and alkoxy-groups are replaced by fluoro.

Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "non-aromatic carbocycle", whether alone or as a suffix or prefix, is intended to mean non-aromatic saturated and unsaturated carbomonocycles, having from 3 to 8 ring carbon atoms, such as cyclopropanyl, cyclopentanyl, cyclohexanyl, cyclopentenyl and cyclohexenyl. If a prefix, such as C3-C6, is given, when said carbocycle comprises the indicated number of carbon atoms, eg. 3, 4, 5 or 6 carbon atoms. Accordingly, "C6 non-aromatic carbocycle" for example includes cyclohexyl and cyclohexenyl. Non-aromatic unsaturated carbocycles are to be distinguished from aryls, as aryl refers to aromatic ring structures, comprising at least one aromatic ring.

As used herein, "cycloalkyl", whether alone or as a suffix or prefix, is intended to mean a saturated carbomonocycle, having from 3 to 8 ring carbon atoms, such as cyclopropanyl, cyclopentanyl and cyclohexanyl. If a prefix, such as C3-C6, is given, when said cycloalkyl comprises the indicated number of carbon atoms, e.g. 3, 4, 5 or 6 carbon atoms. Accordingly, C6 cycloalkyl corresponds to cyclohexyl.

As used herein, "cycloalkenyl", whether alone or as a suffix or prefix, is intended to mean a monounsaturated carbomonocycle, having from 4 to 8 ring carbon atoms, such as cyclopentenyl and cyclohexenyl. If a prefix, such as C3-C6, is given, when said cycloalkenyl comprises the indicated number of carbon atoms, eg. 3, 4, 5 or 6 carbon atoms. Accordingly, C6 cycloalkenyl corresponds to cyclohexenyl.

As used herein, the term "substitutable" refers to an atom to which a hydrogen may be covalently attached, and to which another substituent may be present instead of the hydrogen. A non-limiting example of substitutable atoms include the carbon-atoms of pyridine. The nitrogen-atom of pyridine is not substitutable according to this definition. Further, according to the same definition, the imine nitrogen at position 3 in imidazole is not substitutable, while the amine nitrogen at position 1 is.

As used herein, the term "aryl" refers to a ring structure, comprising at least one aromatic ring, made up of from 5 to 14 carbon atoms. Ring structures containing 5, 6, 7 and 8 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" or "hetaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl or hetaryl groups include monocyclic and bicyclic (e.g., having 2 fused rings) systems. The aromatic ring of the heteroaryl or hetaryl group may be substituted at one or more ring positions.

Examples of heteroaryl or hetaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

As used herein, "non-aromatic heterocycle" refers to a monocycle comprising at least one heteroatom ring member, such as sulfur, oxygen, or nitrogen. Such monocyclic rings may be saturated or unsaturated. However, non-aromatic heterocycles are to be distinguished from heteroaryl groups.

Examples of non-aromatic heterocycle groups include without limitation morpholinyl, piperazinyl, 3H-diazirin-3-yl, oxiranyl, aziridinyl, piperidinyl, pyrrolidinyl, tetrahydrofuranyl, tetrahydropyranyl, dihydro-2H-pyranyl.

As used herein, the term "relative stereochemistry", such as when e.g. referring to e.g. a drawing of a structure, is relating to the relative spatial arrangement of e.g. substituents or groups of a structure. For example, if the relative stereochemistry is indicated by drawing substituents or groups of a molecule in certain directions, the corresponding mirror image of that molecule will have the same relative stereochemistry. On the other hand, if the "absolute stereochemistry" is indicated by drawing substituents or groups of a molecule in certain directions, a particular enantiomer of that molecule is intended.

EMBODIMENTS OF THE INVENTION

Accordingly there is provided, according to one aspect of the invention, a compound, which may be represented with the general formulas (I) or (II)

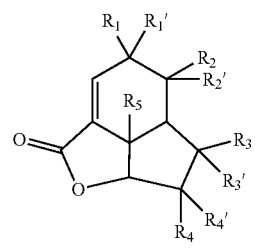

(I)

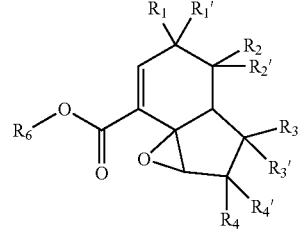

(II)

wherein $R_1$ and $R_1'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl; $R_2$ and $R_2'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl; $R_3$ and $R_3'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl; $R_4$ and $R_4'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N (C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl; $R_5$ is selected from the group consisting of OC0-5 alkyl, OC1-5 fluoroalkyl, OC(O)C1-5 alkyl, OC2-3 alkyleneN(C0-5 alkyl)2 in which the C0-5 alkyl may be the same or different, NHC0-5 alkyl, N(C1-5 alkyl)2 in which the C1-5 alkyl may be the same or different, N(C0-5 alkyl)C(O)C1-5 alkyl, NHaryl, NHheteroaryl, a 3- to 8-membered non-aromatic heterocycle which is connected via a substitutable heteroatom of said non-aromatic heterocycle, SC0-5 alkyl, S(O)C0-5 alkyl, SO2C0-5 alkyl, and N(C0-C3 alkyl)SO2C1-C5 alkyl; $R_6$ is selected from the group consisting of H, C1-5 alkyl, C1-5 fluoroalkyl, and a C3-8 non-aromatic carbocycle; and at least one of $R_2$, $R_2'$, $R_3$, $R_3'$, $R_4$ and $R_4'$ is comprising a carbon atom, an oxygen atom or a nitrogen atom; as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization. Preferably, the compound is a compound according to formula (I).

Compounds according to formula (I), wherein at least one of $R_2$, $R_2'$, $R_3$, $R_3'$, $R_4$ and $R_4'$ comprises a carbon atom, an oxygen atom or a nitrogen atom, have surprisingly been found to be more potent compared to (−)-Galiellalactone in inhibiting IL-6/STAT signaling and especially in inhibiting the proliferation of cancer cells. Further, also the synthetic intermediates according to formula (II), useful to obtain compounds according formula (I), have been found to possess similar biological activities as the corresponding compounds according to formula (I).

The individual diastereomers or enantiomers in a diastereomeric or scalemic mixture, respectively, may be present in the same amount, thus constituting a racemic mixture in the latter case, or in different amounts. However, it is preferred if one of the diastereomers or enantiomers prevails. Accordingly, its is preferred if one of the diastereomers or enantiomers is more than 50%, such as more than 75%, 90%, 95% or even more than 99%.

Preferably, the relative stereochemistry, and even more preferred the absolute stereochemistry, of $R_1$, $R_1'$, $R_2$, $R_2'$, $R_3$, $R_3'$, $R_4$, $R_4'$, $R_5$ and the hydrogen atoms at positions 5a and 7a of a compound of formula (I) is

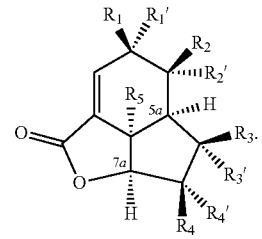

Preferably, the relative stereochemistry, and even more preferred the absolute stereochemistry, of $R_1$, $R_1'$, $R_2$, $R_2'$, $R_3$, $R_3'$, $R_4$, $R_4'$, the hydrogen atom at positions 5a and the oxygen atom at position 7a and 7b of the compound of formula (II) is

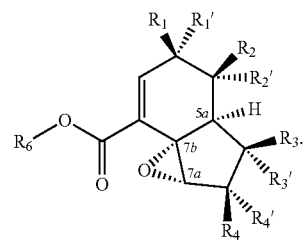

Preferably, any C3-8 non-aromatic carbocycle is cyclohexyl, cyclopentyl or cyclopropyl.

Preferably, any heteroaryl is a 5-membered heteroaryl, such as thiazolyl, furanyl, thiophenyl, pyrrolyl, pyrazolyl, oxazolyl or isooxazolyl, or a 6-membered heteroaryl, such as pyridyl or pyrimidinyl.

Preferably, any 3- to 8-membered non-aromatic heterocycle is piperidinyl, piperazinyl, morpholinyl or pyrrolidinyl. Preferably, these heterocycles are connected via a substitutable nitrogen atom.

Preferably, any aryl is phenyl or naphtalenyl, that may be further substituted with 0 to 4, preferably 0 to 2, substituents. Examples of such substituents include C1-5 alkyl, like methyl or ethyl, C1-5 fluoroalkyl, like trifluoromethyl, halo, like F or Cl, or C0-5 alkyleneOC0-5 alkyl, like CH2OCH3.

Preferably, any halo is fluoro, chloro or bromo.

When $R_5$ is OC0-5 alkyl, the OC0-5 alkyl group is preferably OH.

According to one embodiment, $R_1$, $R_1'$, $R_2$, $R_2'$ $R_3$, $R_3'$, $R_4$ and $R_4'$ of a compound of formula (I) or (II) may be independently selected from the group consisting of H, C1-5 alkyl, aryl, CH2aryl, heteroaryl and CH2heteroaryl. $R_5$ of a compound of formula (I) may be selected from OH, NHC0-5 alkyl, NHaryl and NHheteroaryl. $R_6$ of a compound of formula (II) may be C1-5 alkyl.

According to one embodiment, $R_1$, $R_1'$, $R_2$, $R_2'$ $R_3$, $R_3'$, $R_4$ and $R_4'$ of a compound of formula (I) or (II) may be independently selected from the group consisting of H, C1-5 alkyl, C0-5 alkyleneOC0-5 alkyl, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneC(O)N(C1-5 alkyl)2 in which the C1-5 alkyl may be the same or different, C0-3 alkyleneC(O)OC0-5 alkyl, a 3- to 8-membered non-aromatic heterocycle, C0-3 alkylene aryl and C0-3 alkylene heteroaryl. $R_5$ of a compound of formula (I) may be selected from OC0-5 alkyl, OC(O)C1-5 alkyl, NHC0-5 alkyl, N(C1-5 alkyl)2 in which the C1-5 alkyl may be the same or different, N(C0-5 alkyl)C(O)C1-5 alkyl, NHaryl, and NHheteroaryl. Accordingly, $R_5$ may be OH, OMe, or OC(O)C1-5 alkyl, such as $R_5$ being OH. $R_6$ of a compound of formula (II) may be C1-5 alkyl, such as methyl.

According to one embodiment, at least one of $R_1$, $R_1'$, $R_2$, $R_2'$, $R_3$, $R_3'$, $R_4$ and $R_4'$ of a compound of formula (I) or (II) may be independently selected from the group consisting of C1-5 alkyl, aryl, CH2aryl, heteroaryl and CH2heteroaryl.

According to one embodiment, at least one of $R_2$, $R_2'$, $R_3$, $R_3'$, $R_4$ and $R_4'$ of a compound of formula (I) or (II) may be independently selected from the group consisting of C1-5 alkyl, aryl, CH2aryl, heteroaryl and CH2heteroaryl.

According to one embodiment, at least one of $R_3$, $R_3'$, $R_4$ and $R_4'$ of a compound of formula (I) or (II) may be independently selected from the group consisting of C1-5 alkyl, aryl, CH2aryl, heteroaryl and CH2heteroaryl.

According to one embodiment, at least one of $R_4$ and $R_4'$ of a compound of formula (I) or (II) may be independently selected from the group consisting of C1-5 alkyl, aryl, CH2aryl, heteroaryl and CH2heteroaryl.

According to one embodiment, at least one of $R_1$ and $R_1'$ of a compound of formula (I) or (II) may be independently selected from the group consisting of C1-5 alkyl, such as methyl, aryl, CH2aryl, heteroaryl and CH2heteroaryl. Thus, at least one of $R_1$ and $R_1'$ may be C1-5 alkyl, such as methyl.

According to one embodiment, $R_6$ may be C1-5 alkyl and $R_5$ may be OH, OC1-5 alkyl, OC1-5 fluoroalkyl, or OC(O)C1-5 alkyl.

According to one embodiment, $R_1$ and $R_1'$ of a compound of formula (I) or (II) may be independently selected from the group consisting of H and methyl.

According to one embodiment, $R_1$ and $R_1'$ of a compound of formula (I) or (II) may both be H.

According to one embodiment, one of $R_1$ and $R_1'$ of a compound of formula (I) or (II) may be H and the other one methyl.

According to one embodiment, $R_4$ and $R_4'$ of a compound of formula (I) or (II) may both be H.

According to one embodiment, $R_2$ and $R_2'$ of a compound of formula (I) or (II) may both be H.

According to one embodiment, $R_2$ and $R_2'$ of a compound of formula (I) or (II) may both be methyl.

According to one embodiment, at least one of $R_2$, $R_2'$, $R_3$ and $R_3'$, such as 1, 2, 3 or all 4 of $R_2$, $R_2'$, $R_3$ and $R_3'$, of a compound of formula (I) or (II) may be H.

According to one embodiment, $R_2$, $R_2'$, $R_3$ and $R_3'$ of a compound of formula (I) or (II) may all simultaneously be H.

According to one embodiment, $R_4$ and $R_4'$ of a compound of formula (I) or (II) may be independently selected from the group consisting of H and methyl.

According to one embodiment, $R_5$ of a compound of formula (I) may be OH.

According to one embodiment, $R_6$ of a compound of formula (II) may be C1-5 alkyl, such as methyl.

According to one embodiment, one of $R_1$ or $R_1'$ may be C1-5 alkyl, such as methyl, and the other of $R_1$ or $R_1'$ may be H, all of $R_2$, $R_2'$ $R_3$ and $R_3'$ may be H, one of $R_4$ or $R_4'$ may be methyl, phenyl or benzyl and the other of $R_4$ or $R_4'$ may be H or methyl, $R_5$ may be OH, OC1-5 alkyl, OC1-5 fluoroalkyl, or OC(O)C1-5 alkyl, such as OH, and $R_6$ may be C1-5 alkyl, such as methyl, of a compound of formula (I) or (II).

According to one embodiment, a compound of formula (I) or (II) may be selected from the group consisting of

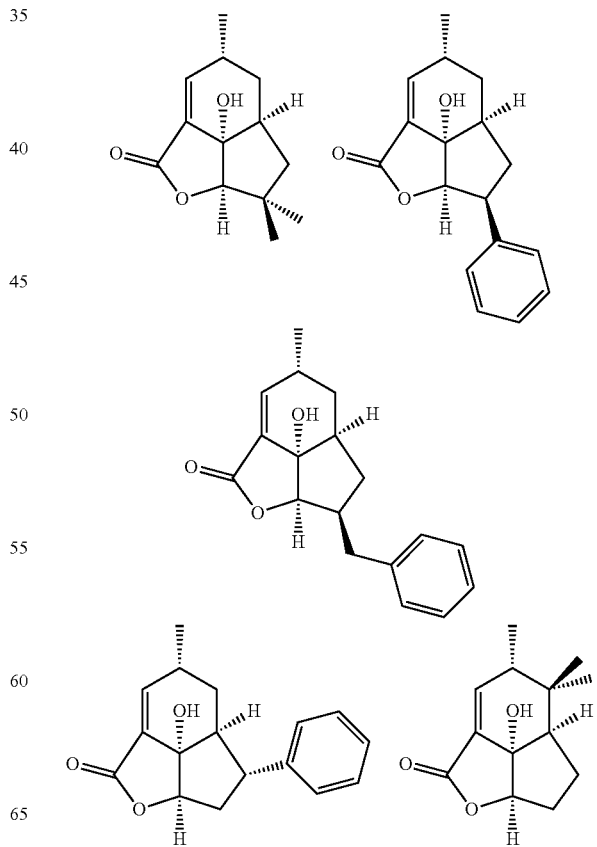

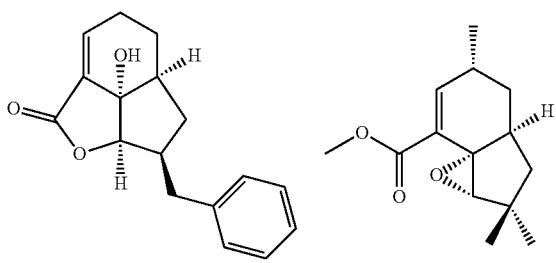
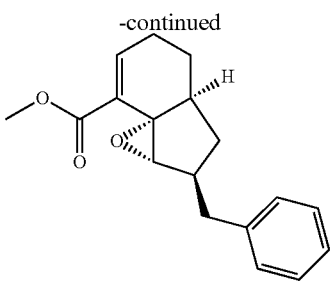
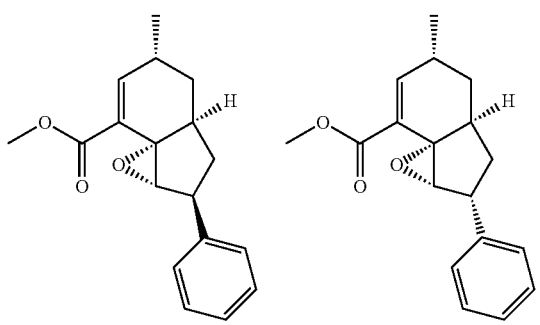
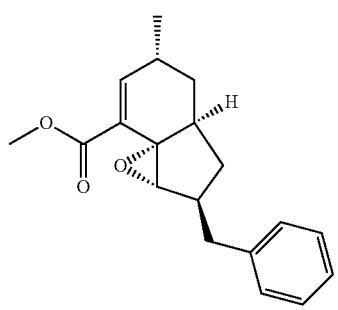
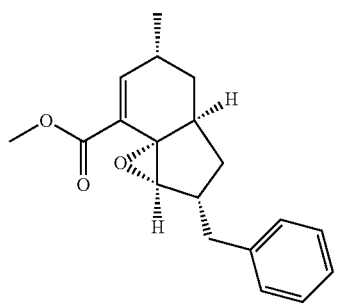
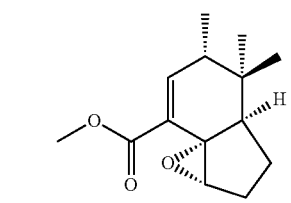
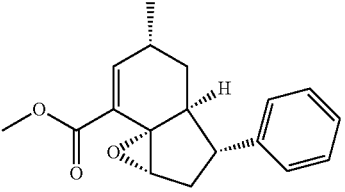

as a mixture of diastereomers, a pure diastereomer, a racemic mixture, a scalemic mixture or a pure enantiomer. Preferably, the compound is a racemic mixture or, more preferred, a pure enantiomer with the above indicated stereochemistry.

According to one embodiment, a compound of formula I or II may be in a crystalline form. For example, such a crystalline form may facilitate the manufacturing of a medicament comprising a compound of formula I or II.

According to one embodiment, there is provided a pharmaceutical composition comprising a compound of formula I or II and at least one pharmaceutically acceptable carrier or excipient. Such a pharmaceutical composition may further comprise one or more different therapeutic agents. Preferably, the one or more different therapeutic agents are selected from a group with a mechanism of action that differs from the mechanism of action of a compound of formula I or II. An advantageous synergistic effect between the therapeutic agents may then occur, allowing a more effective combat of e.g. a disease than if only one of the therapeutic agents is used. Similarly, other therapeutic agents well known in the art, being effective for other diseases and conditions as described herein, may advantageously be used in combination with a compound of formula I or II, in order to e.g. achieve a synergistic effect.

According to one embodiment, there is provided a method for the treatment or prevention of an IL-6/STAT signaling related disorder or an PI3K/NF-κB signaling related disorder, wherein an effective amount of a compound of formula I or II, or an effective amount of a pharmaceutical composition as disclosed herein, is administered to a subject in need of such treatment or prevention.

A pharmaceutical composition according to embodiments disclosed herein may be administered through different routes such as, but not limited to, intravenously, intraperitonealy, intramuscularly, intranasaleously, subcutaneously, sublingually, rectally, orally or through inhalation or insufflation.

The compounds of formula I or II of the invention, or a pharmaceutically acceptable salt or solvate thereof, may be formulated into conventional pharmaceutical compositions, e.g. medicaments. The pharmaceutical composition may comprise a compound of formula I or II in association with a pharmaceutically acceptable carrier or excipient.

A pharmaceutical composition, as described herein, may further comprise pharmaceutically diluents, stabilizers and the like.

The pharmaceutically acceptable carriers may be either solid or liquid. Solid form preparations include, but are not limited to, powders, tablets, dispersible granules, capsules, cachets, and suppositories.

A solid carrier may be one or more substances, which may also act as diluents, flavoring agents, solubilizers, lubricants, suspending agents, binders, or tablet disintegrating agents. A solid carrier may also be an encapsulating material. In powders, the carrier is a finely divided solid, which is in a mixture with a finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient, like a compound of the invention, is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules may be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions may also be formulated in solution in aqueous polyethylene glycol solution.

Aqueous solutions for oral administration may be prepared by dissolving the active component, like a compound of the invention, in water and adding suitable colorants, flavoring agents, stabilizers, and thickening agents as desired. Aqueous suspensions for oral use may be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, or from about 0.10% w to 50% w, of a compound of the invention, all percentages by weight being based on the total weight of the composition.

A therapeutically effective amount for the practice of the present invention may be determined by one of ordinary skill in the art using known criteria including the age, weight and response of the individual patient, and interpreted within the context of the disease which is being treated or which is being prevented.

"Pharmaceutically acceptable" means an excipient that, at the dosage and concentrations employed, does not cause any unwanted effects in the patients to whom it is administered. Such pharmaceutically acceptable excipients are well-known in the art.

A pharmaceutical composition according embodiments herein may be administered to a patient in a pharmaceutically effective dose. By "pharmaceutically effective dose" is meant a dose that is sufficient to produce the desired effects in relation to the condition for which it is administered. The exact dose may be dependent on the activity of the compound, manner of administration, nature and severity of the disorder and/or disease and the general conditions, such as age and body weight of the patient.

According to an embodiment, a compound according to formula I or II, or a pharmaceutical composition comprising a compound of formula I and II, may be used in therapy. Preferably, the compound is a compound according to formula I. Especially, such a compound or composition may be useful in the treatment of an IL-6/STAT signaling related disorder or a PI3K/NF-κB signaling related disorder. Examples of such disorders includes solid cancer, hematological cancer, benign tumor, hyperproliferative disease, inflammation, autoimmune disease, graft or transplant rejection, delayed physiological function of grafts or transplants, neurodegenerative disease or viral infection.

Further, a compound according to formula I or II, or a pharmaceutical composition comprising a compound of formula I and II, may be used for the prevention or treatment of cancer, such as a solid cancers or hematological cancers. Such solid cancers include, but are not limited to, sarcomas, breast cancer, prostate cancer, head and neck cancer, brain tumors, colorectal cancer, lung cancer, pancreatic cancer, cervical cancer, ovarian cancer, melanoma, gastric cancers, renal cell carcinoma, endometrial cancer, sarcomas and hepatocellular carcinomas. Such hematological cancers include, but are not limited to, chronic myelogenous leukemia, acute myelogenous leukemia, cutaneous T-cell lymphoma, Hodgkin's disease, anaplastic large-cell lymphoma and Burkitt's lymphoma.

In addition, a compound according to formula I or II, or a pharmaceutical composition comprising a compound of formula I and II, may be used for the prevention or treatment of benign tumors, including for example Cardiac myxoma and Castleman's disease.

A compound according to the present invention may inhibit proliferation or angiogenesis, induces apoptosis, sensitizes to apoptosis or causes cytotoxicity of cancer cells, including cancer stem cells e.g. leukemic, prostate and breast cancer stem cells. Preferably, the cancer displays elevated or aberrant STAT3 signaling or activity, constitutively phosphorylated or active STAT3 or increased STAT3 protein expression.

According to one embodiment, a compound according to formula I or II, or a pharmaceutical composition comprising a compound of formula I and II, may be used to inhibit the growth or migration of cells. These cells may have elevated or aberrant STAT3 signaling or activity, constitutively phosphorylated or active STAT3 or increased STAT3 protein expression. Hence, associated diseases, such as hyperproliferative diseases, may be treated by a compound according to formula I or II, or a pharmaceutical composition comprising a compound of formula I and II.

According to one embodiment, a compound according to formula I or II, or a pharmaceutical composition comprising a compound of formula I and II, may be used for the prevention or treatment of IL-6 mediated inflammation and/or autoimmune diseases, such as diseases related to the production of acute phase proteins. Diseases which a compound according to formula I or II, or a pharmaceutical composition comprising a compound of formula I and II, may be used for the prevention or treatment of include, but is not limited to, atherosclerosis, diabetes type 2, dementia, osteoporosis, hypertension, coronary artery disease.

According to one embodiment, a compound according to formula I or II, or a pharmaceutical composition comprising a compound of formula I and II, may be used for the prevention or treatment of inflammatory and/or autoimmune diseases including, but not limited to, arthritis, Crohn's disease, ulcerative colitis, rheumatoid arthritis, inflammatory bowel diseases, asthma, allergy, atopic dermatitis, systemic lupus erythematosus, uveitis and COPD. In addition, compounds of the invention may be used for the suppression of graft and transplant rejection, or for improved onset of the physiological functions of such grafts and transplants after transplantation.

According to one embodiment, a compound according to formula I or II, or a pharmaceutical composition comprising a compound of formula I and II, may be used for the prevention or treatment of inflammatory, autoimmune and neurodegenerative diseases affecting the CNS including, but not limited to, Parkinson's disease, Alzheimer's disease, multiple sclerosis, stroke and ischemia reperfusion injury.

According to one embodiment, a compound according to formula I or II, or a pharmaceutical composition comprising a compound of formula I and II, may be used for the prevention or treatment of chronic viral infections including, but not limited to, hepatitis C, herpes, infections caused by Kaposis Sarcoma-associated herpes virus (KSHV) and Epstein-Barr virus related infections.

According to one embodiment, a compound according to formula I or II, or a pharmaceutical composition comprising a compound of formula I and II, may be used for the prevention or treatment of hyperproliferative diseases including, but not limited to, psoriasis.

The dose required for the therapeutic or preventive treatment of a particular disorder will necessarily be varied depending on the host treated, the route of administration and the severity of the illness being treated.

Evidently, a compound according to formula I or II, or a pharmaceutical composition comprising a compound of formula I or II as disclosed herein, may used for the manufacture of a medicament for use in such treatment as disclosed herein.

Further, a compound according to formula I or II, or a pharmaceutical composition comprising a compound of formula I and II, may be used in method for treating or preventing of such disorders as disclosed herein. Such a method may include the step of administering an effective amount of a compound of formula I or II, or an effective amount of a pharmaceutical composition as disclosed herein, to a subject suffering from such a disorder.

In the context of the present specification, the term "therapy" and "treatment" includes prevention or prophylaxis, unless there are specific indications to the contrary. The terms "therapeutic" and "therapeutically" should be construed accordingly.

According to one embodiment, treatment does also encompass pre-treatment, i.e. prophylactic treatment.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

According to one embodiment, a compound according to formula I or II, or a pharmaceutical composition comprising a compound of formula I and II, may be used as a monotherapy for the treatment of various diseases or conditions. Such diseases or conditions include, for example, diseases or conditions related to elevated or aberrant IL-6/STAT signaling and/or PI3K/NF-κB signaling, such as cancer.

According to one embodiment, a compound according to formula I or II, or a pharmaceutical composition comprising a compound of formula I and II, may be used in combination with other treatments or therapies, in particular cancer therapies, including chemotherapy, radiation therapy, gene therapy, cell therapy and surgery. In addition, a compound according to formula I or II, or a pharmaceutical composition comprising a compound of formula I and II, may enhance anti-tumor immune mediated cytotoxicity. Hence, synergistic effects between a compound according to formula I or II, and another treatment or therapy or a immune mediated response, may favorably occur.

According to one embodiment, a pharmaceutical composition according to embodiments herein may be administered alone or in combination with other therapeutic agents. These agents may be incorporated as part of the same pharmaceutical composition or may be administered separately. It is well known in the art that a combination of mechanistically unrelated therapeutic agents in the same medicament may have beneficial effects in the treatment of conditions or diseases characterized by e.g. abnormal immune regulation, abnormal hematopoiesis, inflammation or oncogenesis. Examples of other therapeutic agents include, but is not limited to, anti-cancer agents such as Abraxane, Aldesleukin, Alemtuzumab, Aminolevulinic Acid, Anastrozole, Aprepitant, Arsenic Trioxide, Azacitidine, Bendamustine Hydrochloride, Bevacizumab, Bexarotene, Bortezomib, Bleomycin, Cabazitaxel, Capecitabine, Carboplatin, Cetuximab, Cisplatin, Clofarabine, Cyclophosphamide, Cytarabine, Dacarbazine, Dasatinib, Daunorubicin Hydrochloride, Decitabine, Degarelix, Denileukin Diftitox, Dexrazoxane Hydrochloride, Docetaxel, Doxorubicin Hydrochloride, Doxorubicin Hydrochloride Liposome, Eltrombopag Olamine, Epirubicin Hydrochloride, Erlotinib Hydrochloride, Etoposide, Etoposide Phosphate, Everolimus, Exemestane, Filgrastim, Fludarabine Phosphate, Fluorouracil, Fulvestrant, Gefitinib, Gemcitabine Hydrochloride, Ibritumomab Tiuxetan, Imatinib Mesylate, Imiquimod, Irinotecan Hydrochloride, Ixabepilone, Lapatinib Ditosylate, Lenalidomide, Letrozole, Leucovorin Calcium, Leuprolide Acetate, Liposomal Cytarabine, Methotrexate, Nelarabine, Nilotinib, Ofatumumab, Oxaliplatin, Paclitaxel, Palifermin, Palonosetron Hydrochloride, Panitumumab, Pazopanib Hydrochloride, Pegaspargase, Pemetrexed Disodium, Plerixafor, Pralatrexate, Raloxifene Hydrochloride, Rasburicase, Recombinant HPV Bivalent Vaccine, Recombinant HPV Quadrivalent Vaccine, Rituximab, Romidepsin, Romiplostim, Sipuleucel-T, Sorafenib Tosylate, Sunitinib Malate, Talc, Tamoxifen Citrate, Temozolomide, Temsirolimus, Thalidomide, Topotecan Hydrochloride, Toremifene, Tositumomab and I 131 Iodine Tositumomab, Trastuzumab, Vincristine Sulfate, Vorinostat and Zoledronic Acid, or the like.

When a compound according to embodiments disclosed herein is combined with at least another therapeutic agent, such as an anti-cancer agent, in a pharmaceutical composition, such as a medicament, a therapeutically effective dose of the pharmaceutical composition may comprise 1 to 10 times less than the respective established therapeutically effective dose of a component, i.e. a compound according to the invention or the therapeutic agent, when administered alone for prevention or treatment of the same disease or condition.

Accordingly, by combining a compound according to embodiments disclosed herein with another therapeutic agent, such as an anti-cancer agent, it may be possible to achieve synergistic effects compared to if only a compound according to the present invention, or the other therapeutic agent, were administrated alone.

For example, a compound according to formula I or II may be used for reversing drug resistance and/or enhancing effects of anti cancer agents, thus offering the possibility of lowering the dose of the anticancer agent to avoid side-effects and/or enhancing the efficacy.

According to one embodiment, a compound according to formula I or II, or a pharmaceutical composition comprising a compound of formula I and II, may be used for the treatment of various diseases or conditions in humans or animals, such as dogs, cats, horses, cows or other mammals, in particular domestic animals. Animals may be treated for the same diseases and conditions as humans may be treated for.

According to one embodiment, compounds according to formula (I) or (II) may also be useful as pharmacological tools in the development and standardisation of in-vitro and in-vivo test systems for the evaluation of other compounds with similar activity. Such in-vivo test systems include tests in laboratory animals such as cats, dogs, rabbits, monkeys, pigs, goats, guinea pigs, rats and mice. Furthermore, compounds of formula (I) or (II) may be used as molecular probes to identify and/or locate the target of their action, such as targets of relevance for IL-6/STAT signaling and/or PI3K/NF-κB signaling, as well as employed as a diagnostic tool for diagnosis of a disease or condition in-vivo, ex-vivo or in-vitro, or as synthetic precursors to such probes. Molecular probes of formula (I) or (II) may include reactive, labeled, i.e. compounds of formula (I) or (II) wherein one or several of the composing atoms have been enriched with a radioactive or by other means detectable isotope, and fluorescent compounds as well known to the one skilled in the art. Hence, compounds according to formula (I) or (II) may include compounds wherein one or several atoms have been substituted with heavier isotopes, such as substitution of hydrogen for deuterium, carbon-12 for carbon-13 or carbon-14, and/or nitrogen-14 for nitrogen-15.

Although various selections, within the interval given for each of the different groups of formula (I) or (II), have been described individually above as various possible embodiments, any combination of these selections is also possible.

Accordingly, other embodiments of the invention relates to a compound according to formula (I) or (II), wherein at least two different groups, such as 2, 3, 4, 5, or further different groups, of formula (I) or (II) are to be selected from the various selections, within the interval given for each of the different groups of formula (I) or (II), disclosed herein.

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality.

Another embodiment of the present invention relates to a process for preparing a compound according to formula (I) or (II) as a free base, acid, or salts thereof. Further, additionally embodiments relate to synthetic intermediates, which are useful in the synthesis of a compound of formula (I) or (II) as a free base, acid, or salts thereof. Specific and generic examples of such intermediates are given below. Further, such intermediates may include compounds according to formula (I) or (II), which may be used to produce another compound according to formula (I) or (II).

Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are well known within the art. Further such procedures and groups are described in the literature, such as in "Protective Groups in Organic Synthesis", 3rd ed., T. W. Green, P. G. M. Wuts, Wiley-Interscience, New York (1999).

It is also to be understood that a transformation of a group or substituent into another group or substituent by chemical manipulation may be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Examples of transformations are given below, and it is to be understood that the described transformations are not limited only to the generic groups or substituents for which the transformations are exemplified.

References and descriptions on other suitable transformations are for example given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry well known to the one skilled in the art, such as "March's Advanced Organic Chemistry", 5th ed., M. B. Smith, J. March, John Wiley & Sons (2001) or, "Organic Synthesis", 2nd ed., M. B. Smith, McGraw-Hill, (2002).

Techniques for purification of intermediates and final products include for example, straight and reversed phase chromatography on column or rotating plate, size exclusion chromatography, recrystallisation, distillation and liquid-liquid or solid-liquid extraction, which will be readily understood by the one skilled in the art.

The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves may be used for the heating of reaction mixtures.

The terms "flash chromatography" or "flash column chromatography" shall mean preparative chromatography on silica using an organic solvent, or mixtures thereof, as mobile phase.

In the various schemes given below, generic groups, such as R-groups, have the same representation as given above herein, if not specifically defined.

In the various schemes given below, the indicated stereochemistry is intended to mean relative stereochemistry, unless noted otherwise.

Methods of Preparation of Final Compounds of Formula (II) by Epoxidation of Intermediate (III) (Scheme 1)

Scheme 1. Examples of non-limiting methods for the preparation of final compounds of formula (II), by epoxidation of a compound according to formula (II) as disclosed herein.

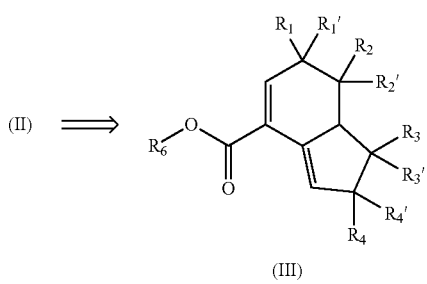

The preparation of final compounds of formula (II) may be achieved by regio- and stereoselective epoxidation of the electron rich double bond of intermediates (III) using mCPBA, dimethyldioxirane, trifluoromethyldioxirane, peracids or the like.

Methods of Preparation of Final Compounds of Formula (I) by Lactonization Scheme 2)

Scheme 2. Examples of non-limiting methods for the preparation of final compounds of formula (I) as disclosed herein, by hydrolysis and lactonization of a compound of formula (II) as disclosed herein.

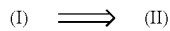

Ester hydrolysis, under of basic or acidic conditions, of (II) followed by acid catalyzed epoxide opening and subsequent lactonization yields the final lactone compound (I).

Methods of Preparation of Tetrahydroindene Intermediates of Formula (III) by an Intramolecular [4+2] Vinylallene Diels-Alder Cycloaddition (Scheme 3)

Scheme 3.

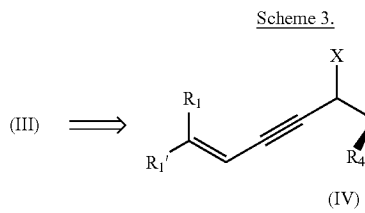

X is a leaving group such as, but not limited to, halogen, mesylate, toslylate, carbonate, acetate. Intermediate (IV) is treated with a Pd(0) source, or alternatively Pd(0) may be formed in situ from Pd(II), together with a suitable ligand, preferably a bidenate ligand such as Xantphos, DPPP, at room temperature or at an elevated temperature using conventional heating or microwave heating, under a CO atmosphere of 1 bar to 10 bar in a suitable solvent, e.g. toluene, together with an alcohol $R_6OH$. CO may be used from a gas tube or formed in situ from e.g. $Mo(CO)_6$.

Methods of Preparation of Tetrahydroindene Intermediates of Formula (IV) (Scheme 4)

Scheme 4

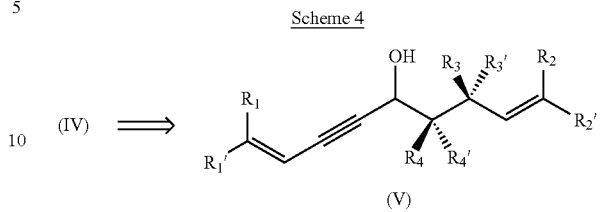

Intermediates of structure (IV) where X is a leaving group may be prepared by converting the hydroxyl group of intermediate (V) to a X. This may be done by treating (V) with an acylating reagent in the presence of a base or a halogenating agent.

Methods of Preparation of Intermediates of Formula (V) (Scheme 6)

Scheme 6.

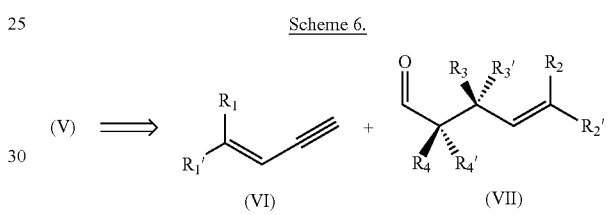

Intermediates of formula (V) may be prepared by the addition of alkynes to aldehydes. Alkynes (VI) may be converted to nucleophilic metal acetylides e.g. by deprotonation of the alkyne with a suitable base, e.g. n-BuLi, to make the corresponding metal acetylide. These nucleophilic alkynes may then react with aldehydes of formula (VII).

Methods of Preparation of Intermediates of Formula (V) (Scheme 7)

Scheme 7.

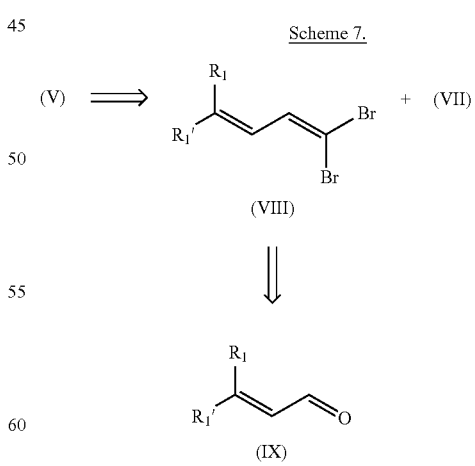

A lithium acetylide nucleophile may be formed in situ by the treatment of dibromo alkenes (VIII) with n-BuLi. The acetylide may add directly to an aldehyde (VII) to form intermediate (V).

Methods of Preparation of Intermediates of Formula (VI) (Scheme 8)

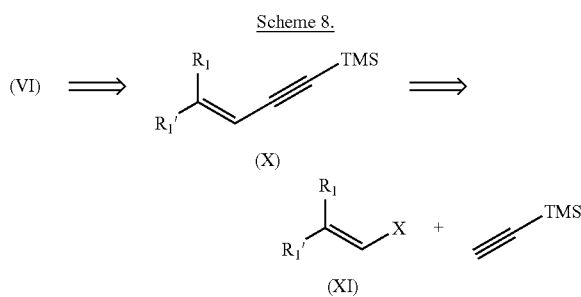

Vinyl acetylenes of formula (X) may be prepared from trimethylsilyl acetylene and readily available vinyl intermediates of formula (XI), where X is a halogen or triflate, through a palladium catalyzed Sonogashira coupling. After the coupling the trimethylsilyl group is removed to afford intermediate (VI).

Methods of Preparation of Intermediates of Formula (V) (Scheme 9)

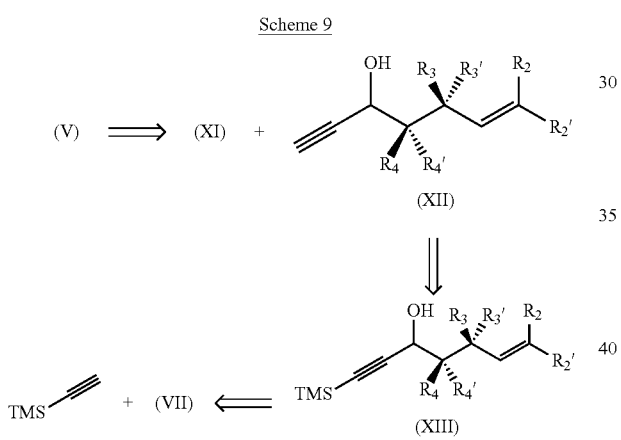

Intermediates of formula (V) may be prepared through a palladium catalyzed Sonogashira coupling with readily available vinyl intermediates of formula (XI), where X is a halogen or triflate, and an intermediate propargyl alcohol of formula (XII). Propargyl alcohols of formula (XII) may be prepared by the addition of trimethylsilyl acetylene to an aldehyde (VII) and subsequent desilylation.

Methods of Preparation of Intermediate Aldehydes of Formula (VII) (Scheme 10)

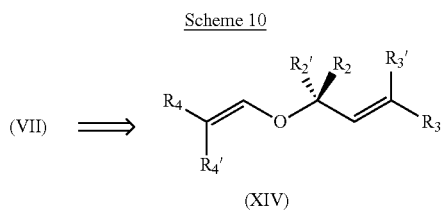

Intermediate aldehydes of formula (VII) may be prepared from vinyl allyl ethers (XIV) through a Claisen rearrangement. The Claisen rearrangement may be thermal or catalyzed by a Lewis acid. Vinyl allyl ethers (XIV) are commonly prepared by reacting an allylic alcohol with an alkyl vinyl ether in the presence of a catalytic amount of a protic or Lewis acid.

Methods of Preparation of Intermediate Aldehydes of Formula (VII) (Scheme 11)

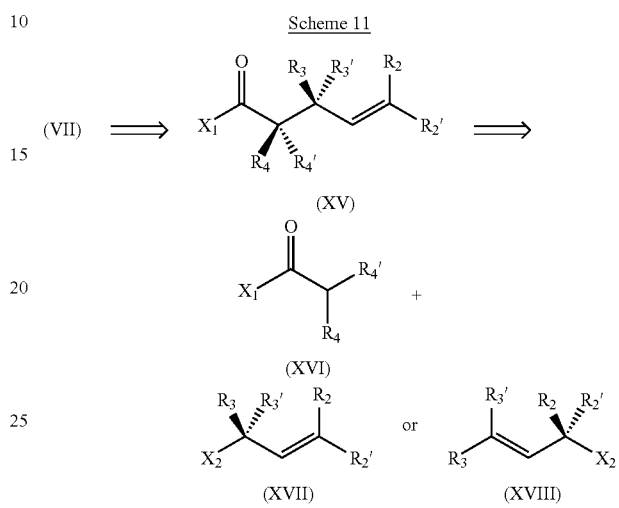

Aldehydes of formula (VII) may be prepared by the reduction of the corresponding ester (XV, $X_1$=Oalkyl) or amide (XV, $X_1$=$NR_2$). The reduction may be directly to the adehyde or via reduction to the corresponding alcohol and subsequent oxidation. Intermediates of formula (XV) may be prepared by alkylation of amides or esters of formula (XVI) using a suitable base and reactive alkylation reagents such as (XVII) or (XVIII) where $X_2$ is a good leaving group such as a halogen or acetate.

COMPOUND EXAMPLES

Abbreviations

DMF N,N'-Dimethylformamide
THF Tetrahydrofurane
sat. Saturated
h hour
r.t. room temperature
eq, equiv equivalents
quant quantitative
aq aqueous
Ph phenyl
mCPBA meta-Chloroperoxybenzoic acid
OAc acetate
DPPP 1,3-Bis(diphenylphosphino)propane
Me Methyl
Et Ethyl Preparation of Intermediates Below follows non-limiting examples on the synthesis of intermediates useful for the preparation of compounds of formula I or II.

Preparation of Final Compounds

Below follows non-limiting examples on the synthesis of final compounds of formula I or II.

General Methods

All materials were obtained from commercial sources and were used without further purification unless otherwise noted. THF was distilled from sodium/benzophenone ketyl under $N_2$, toluene was distilled from $CaH_2$ under $N_2$. All reactions were carried out in standard dry glassware and atmospheric surroundings unless otherwise stated. Thin layer chromatography (TLC) was carried out on Merck precoated silica gel aluminum sheets (60 $F_{254}$), detected under UV light and visualized with anisaldehyde/sulfuric acid or PMA. Column chromatography was performed on $SiO_2$ (Matrex LC-gel: 60A, 35-70 MY, Grace). $^1H$ and $^{13}C$ NMR spectra were recorded using a Bruker DR400 at room temperature. Chemical shifts are given in ppm relative to TMS using the residual solvent signal of $CDCl_3$ as internal standard (7.27 and 77.23 respectively) Mass spectra were recorded on a JEOL JMDX 303 spectrometer.

Scheme 12

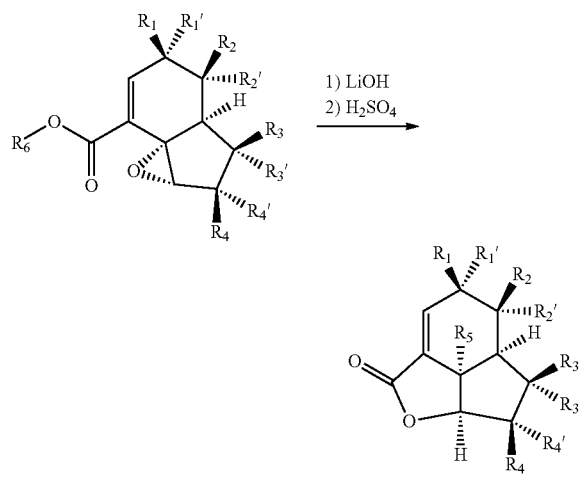

General method for the preparation of lactones corresponding to compounds of formula (I) (scheme 12).

$LiOH.H_2O$ (1.2 equiv) was added to a solution of the epoxide (1.0 equiv) in $THF/H_2O$ 1:1. The solution was stirred for 5 h when additional $LiOH.H_2O$ (1.2 equiv) was added. After stirring for 7.5 h the solution was diluted with THF and 10% $H_2SO_4$ was added. The solution was stirred for 3 days before being diluted with diethyl ether. The phases were separated and the organic phase was washed with $NaHCO_3$ (sat), dried ($MgSO_4$) and concentrated. Flashchromatography ($SiO_2$, heptane/EtOAc 2:1), unless otherwise noted, afforded the desired product.

Example 1

2a$^1$-hydroxy-4,7,7-trimethyl-4,5,5a,6,7,7a-hexahydroindeno[1,7-bc]furan-2(2a$^1$H)-one

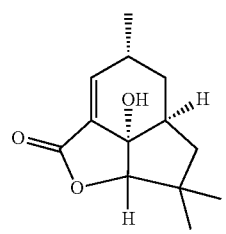

$^1H$ NMR ($CDCl_3$) δ 6.91 (1H, d, J=3.8 Hz), 4.30 (1H, s), 2.49 (1H, m), 2.43 (1H, m), 2.11 (1H, m), 1.87 (1H, ddd, J=14.6, 6.5 and 2.4 Hz), 1.63 (1H, dd, J=10.0 and 4.2 Hz), 1.57 (1H, dd, J=10.2 and 4.1 Hz), 1.45 (1H, dd, J=13.2 and 6.9 Hz), 1.22 (3H, d, J=7.2 Hz), 1.17 (3H, s), 0.91 (3H, s)

$^{13}C$ NMR ($CDCl_3$) δ 170.1, 146.8, 128.7, 107.2, 95.3, 80.5, 41.9, 39.9, 39.1, 30.0, 29.3, 28.0, 24.7, 19.8

HRMS calcd for $C_{13}H_{19}O_3$ [M+1]: 223.1334. found: 223.1345.

Example 2

2a$^1$-hydroxy-4-methyl-7-phenyl-4,5,5a,6,7,7a-hexahydroindeno[1,7-bc]furan-2(2a$^1$H)-one

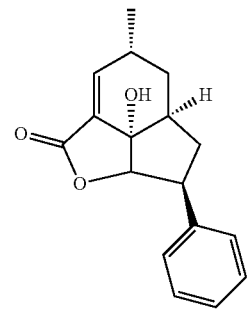

$^1H$ NMR ($CDCl_3$) δ 7.31 (2H, m), 7.22 (1H, m), 7.06 (2H, d, J=7.3 Hz), 7.01 (1H, d, J=3.9 Hz), 4.93 (1H, d, J=8.5 Hz), 3.53 (1H, dt, J=12.5 and 7.9 Hz), 2.56 (1H, m), 2.50 (1H, m), 2.00 (2H, m), 1.73 (1H, ddd, J=14.3, 10.0 and 4.3 Hz), 1.60 (1H, q, J=12.5 Hz), 1.27 (3H, d, J=7.2 Hz)

$^{13}C$ NMR ($CDCl_3$) δ 170.1, 147.2, 137.1, 128.9, 128.8, 128.6, 127.2, 88.9, 82.8, 80.1, 47.4, 41.1, 33.7, 29.6, 27.9, 19.9

HRMS calcd for $C_{17}H_{18}O_3Na$ [M+1]: 293.1154. found: 293.1147.

Example 3

7-benzyl-2a$^1$-hydroxy-4-methyl-4,5,5a,6,7,7a-hexahydroindeno[1,7-bc]furan-2(2a$^1$H)-one

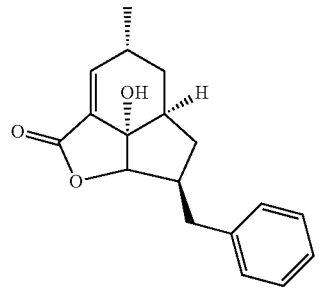

$^1H$ NMR ($CDCl_3$) δ 7.27 (2H, m), 7.18 (3H, m), 6.93 (1H, d, J=3.8 Hz), 4.77 (1H, d, J=8.2 Hz), 2.85 (1H, dd, J=13.7 and 6.7 Hz), 2.52 (1H, m), 2.44 (1H, m), 2.36 (1H, dd, J=13.7 and 8.7 Hz), 2.28 (1H, m), 1.85 (1H, ddd, J=14.6, 6.6 and 2.4 Hz), 1.64 (2H, m), 1.22 (3H, d, J=7.2 Hz), 1.01 (1H, q, J=12.3 Hz)

$^{13}C$ NMR ($CDCl_3$) δ 171.0, 147.2, 140.4, 128.9, 128.8, 128.6, 126.3, 89.3, 80.1, 43.3, 41.1, 35.6, 33.7, 29.5, 27.8, 19.8

HRMS calcd for $C_{18}H_{21}O_3$ [M+1]: 285.1491. found: 285.1490.

Example 4

5,5a,6,7,7a,7b-hexahydro-7b-hydroxy-4-methyl-6-phenyl-indeno[1,7-bc]furan-2(4H)-one

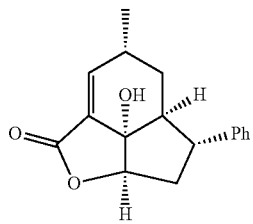

Obtained as faint yellow crystals in 26% yield after flash chromatography using heptane/EtOAc (2:1) as eluent and subsequent trituration using n-hexane from 2-propanol.

$^1$H NMR (CDCl$_3$) δ 7.33 (2H, m), 7.25 (1H, m), 7.17 (2H, m), 6.99 (1H, d, J=3.9 Hz), 4.98 (1H, dd, J=8.6 and 1.6 Hz), 3.23 (1H, bs), 2.72 (1H, dt, J=11.5 and 8.1 Hz), 2.50 (2H, m), 2.25 (1H, ddd, J=15.5, 11.2 and 8.6 Hz), 2.16 (1H, ddd, J=15.5, 8.0 and 1.5 Hz), 1.76 (1H, ddd, J=14.7, 6.6 and 2.4 Hz), 1.60 (1H, ddd, J=14.7, 9.8 and 4.3 Hz), 1.23 (3H, d, J=7.2 Hz)

$^{13}$C NMR (CDCl$_3$) δ 171.0, 147.6, 141.5, 129.4, 129.0, 127.5, 127.2, 87.8, 79.8, 49.0, 44.9, 39.4, 29.5, 26.2, 19.7

HRMS calcd for $C_{17}H_{18}O_3Na$ [M+Na]: 293.1154. found: 293.1148.

Example 5

5,5a,6,7,7a,7b-hexahydro-7b-hydroxy-4,5,5-trimethyl-indeno[1,7-bc]furan-2(4H)-one

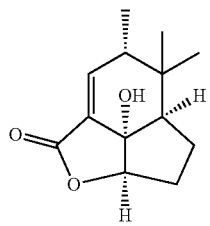

Obtained as white crystals in 9% yield after flash chromatography using heptane/EtOAc (2:1) as eluent and subsequent trituration with n-hexane from 2-propanol.

$^1$H NMR (CDCl$_3$) δ 6.75 (1H, dd, J=3.4 and 1.2 Hz), 4.78 (1H, dd, J=9.2 and 2.1 Hz), 2.45 (1H, bs), 2.28 (1H, m), 2.12 (2H, m), 1.78 (1H, m), 1.67 (1H, dd, J=15.7 and 9.0 Hz), 1.35 (1H, m), 1.17 (3H, d, J=7.5 Hz), 1.11 (3H, s), 1.00 (3H, s)

$^{13}$C NMR (CDCl$_3$) δ 170.5, 146.6, 128.1, 90.8, 81.2, 53.1, 39.8, 33.5, 28.6, 27.7, 25.4, 24.8, 13.1

HRMS calcd for $C_{13}H_{19}O_3$ [M+1]: 223.1334. found: 223.1339.

Example 6

5,5a,6,7,7a,7b-hexahydro-7b-hydroxy-7-benzyl-indeno[1,7-bc]furan-2(4H)-one

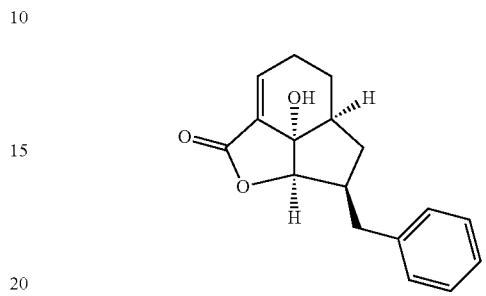

Obtained after flash chromatography (heptane: EtOAc, 10:1) in 37% yield.

Recrystallised from i-propanol: ether to give cream crystals.

$^1$H NMR (CDCl$_3$) δ 7.27 (2H, m), 7.18 (3H, m), 7.10 (1H, dd, J$_1$=4.8 Hz and J$_2$=3.2 Hz), 4.75 (1H, d, J=7.92 Hz), 3.25 (1H, bs), 2.84 (1H, dd, dd, J$_1$=13.6 Hz and J$_2$=6.8 Hz), 2.52 (1H, m), 2.45 (1H, dt, J$_1$=7.9 Hz and J$_2$=2.8 Hz), 2.35 (1H, dd, J$_1$=13.7 Hz and J$_2$=8.6 Hz), 2.30 (1H, m), 2.26 (1H, m) 2.02 (1H, m) 1.63 (2H, m) 0.93 (1H, q, J$_1$=12.4 Hz)

$^{13}$C NMR (CDCl$_3$) δ 143.0, 140.2, 129.6, 128.7, 128.4, 126.1, 89.2, 80.1, 43.5, 39.9, 35.8, 34.2, 22.6, 18.7

HRMS calc δ for $C_{17}H_{18}O_3$ [M+1]: 271,1334 found: 271.1339

Scheme 13

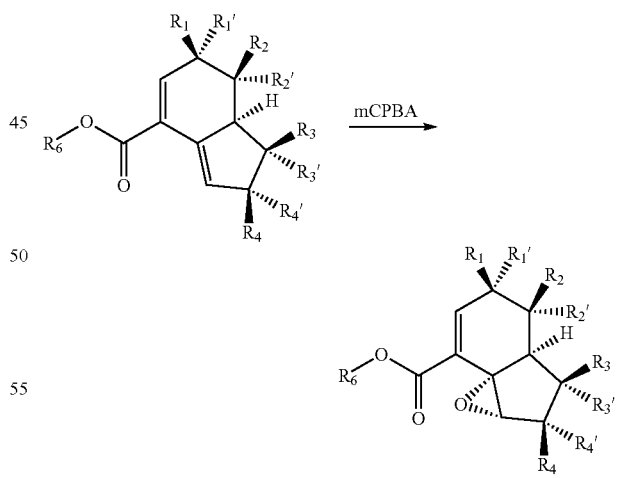

General method for the preparation of epoxides corresponding to compounds of formula (II) (scheme 13).

mCPBA (70%, 1.3 eq) was added to a solution of the corresponding tetrahydroindene (1.0 eq) in CH$_2$Cl$_2$ at 0° C. The mixture was stirred at 0° C. for 40 min. A saturated aqueous solution of Na$_2$S$_2$O$_3$ was added and the phases separated. The organic phase was washed with NaHCO$_3$ (sat.), dried (MgSO$_4$) and concentrated. Flashchromatography (SiO$_2$, hexane/ether 10:1), unless otherwise noted, afforded to desired product.

Example 7 methyl 5-methyl-2-phenyl-1a,2,3,3a,4,5-hexahydroindeno[1,7a-b]oxirene-7-carboxylate

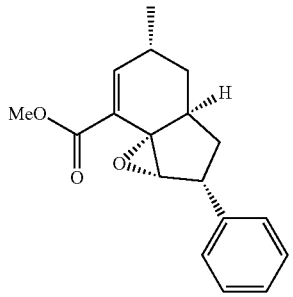 [SMILES: COC(=O)C1=C[C@H](C)C[C@H]2C[C@H](c3ccccc3)[C@@H]3O[C@]123]

$^1$H NMR (CDCl$_3$) δ 7.32 (3H, m), 7.27 (2H, m), 7.19 (2H, m), 4.57 (1H, s), 3.75 (3H, s), 3.55 (1H, t, J=4.7 Hz), 2.80 (1H, m), 2.56 (1H, m), 2.24 (1H, m), 1.87 (1H, m), 1.63 (2H, m), 1.16 (3H, d, J=7.4 Hz)

$^{13}$C NMR (CDCl$_3$) δ 165.5, 154.8, 142.2, 128.9, 127.7, 126.7, 125.9, 66.3, 64.1, 51.9, 45.2, 33.5, 32.9, 31.8, 30.2, 19.6

HRMS calcd for C$_{18}$H$_{20}$O$_3$ [M+1]: 285.1491. found: 285.1486.

Example 8 methyl 5-methyl-2-phenyl-1a,2,3,3a,4,5-hexahydroindeno[1,7a-b]oxirene-7-carboxylate

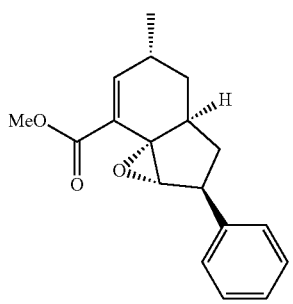 [SMILES: COC(=O)C1=C[C@H](C)C[C@H]2C[C@@H](c3ccccc3)[C@@H]3O[C@]123]

$^1$H NMR (CDCl$_3$) δ 7.42 (2H, m), 7.31 (3H, m), 7.25 (1H, m), 4.56 (1H, s), 3.72 (3H, s), 3.19 (1H, dd, J=10.5 and 7.2 Hz), 2.80 (1H, m), 2.20 (1H, m), 1.91 (2H, m), 1.68 (1H, dd, J=13.0 and 3.2 Hz), 1.31 (1H, dt, J=12.0 and 10.6 Hz), 1.19 (3H, d, J=7.5 Hz)

$^{13}$C NMR (CDCl$_3$) δ 165.6, 154.4, 141.8, 128.6, 127.9, 126.8, 126.1, 66.8, 62.2, 51.9, 46.5, 36.1, 32.4, 31.5, 30.2, 19.5

HRMS calcd for C$_{18}$H$_{20}$O$_3$ [M+1]: 285.1491. found: 285.1493.

Example 9 methyl 2-benzyl-5-methyl-1a,2,3,3a,4,5-hexahydroindeno[1,7a-b]oxirene-7-carboxylate

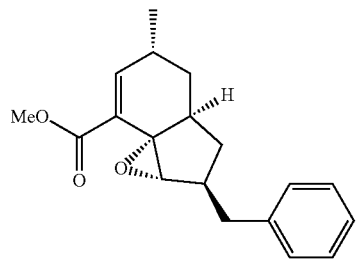 [SMILES: COC(=O)C1=C[C@H](C)C[C@H]2C[C@@H](Cc3ccccc3)[C@@H]3O[C@]123]

$^1$H NMR (CDCl$_3$) δ 7.29 (2H, m), 7.22 (4H, m), 4.26 (1H, s), 3.70 (3H, s), 2.89 (1H, dd, J=13.4 and 7.8 Hz), 2.73 (2H, m), 2.29 (1H, m), 2.29 (1H, m), 2.01 (1H, m), 1.83 (1H, dt, J=13.0 and 6.3 Hz), 1.68 (1H, m), 1.53 (1H, m), 1.14 (3H, d, J=7.4 Hz), 0.10 (1H, m)

$^{13}$C NMR (CDCl$_3$) δ 165.6, 154.2, 141.2, 129.2, 129.0, 128.6, 126.1, 65.7, 63.2, 51.8, 43.1, 37.3, 35.6, 31.5, 30.3, 30.1, 19.5

HRMS calcd for C$_{19}$H$_{23}$O$_3$ [M+1]: 299.1647. found: 299.1659.

Example 10 methyl 2-benzyl-5-methyl-1a,2,3,3a,4,5-hexahydroindeno[1,7a-b]oxirene-7-carboxylate

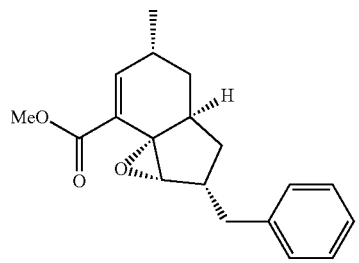 [SMILES: COC(=O)C1=C[C@H](C)C[C@H]2C[C@H](Cc3ccccc3)[C@@H]3O[C@]123]

$^1$H NMR (CDCl$_3$) δ 7.31 (2H, m), 7.22 (4H, m), 4.31 (1H, s), 3.74 (3H, s), 2.73 (2H, m), 2.61 (1H, m), 2.54 (1H, dd, J=12.6 and 8.2 Hz), 2.00 (1H, m), 1.79 (1H, dt, J=13.0 and 6.3 Hz), 1.58 (1H, dd, J=3.2 Hz), 1.39 (1H, dd, J=12.6 and 7.4 Hz), 1.22 (1H, m), 1.14 (3H, d, J=7.4 Hz)

$^{13}$C NMR (CDCl$_3$) δ 165.6, 154.3, 140.2, 129.2, 129.0, 128.7, 126.3, 66.8, 63.3, 51.8, 41.7, 36.8, 33.1, 31.8, 30.3, 28.8, 19.5

HRMS calcd for C$_{19}$H$_{23}$O$_3$ [M+1]: 299.1647. found: 299.1635.

Example 11 methyl 2,2,5-trimethyl-1a,2,3,3a,4,5-hexahydroindeno[1,7a-b]oxirene-7-carboxylate

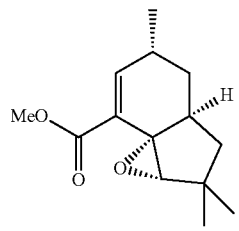 [SMILES: COC(=O)C1=C[C@H](C)C[C@H]2CC(C)(C)[C@@H]3O[C@]123]

$^1$H NMR (CDCl$_3$) δ 6.91 (1H, d, J=3.8 Hz), 4.30 (1H, s), 2.49 (1H, m), 2.43 (1H, m), 2.11 (1H, m), 1.87 (1H, ddd, J=14.6, 6.5 and 2.4 Hz), 1.63 (1H, dd, J=10.0 and 4.2 Hz), 1.57 (1H, dd, J=10.2 and 4.1 Hz), 1.45 (1H, dd, J=13.2 and 6.9 Hz), 1.22 (3H, d, J=7.2 Hz), 1.17 (3H, s), 0.91 (3H, s)
$^{13}$C NMR (CDCl$_3$) δ 170.1, 146.8, 128.7, 107.2, 95.3, 80.5, 41.9, 39.9, 39.1, 30.0, 29.3, 28.0, 24.7, 19.8
HRMS calcd for C$_{13}$H$_{19}$O$_3$ [M+1]: 223.1334. found: 223.1345.

Example 12

Methyl 1a,2,3,3a,4,5-hexahydro-5-methyl-3-phenyl-indeno[1,7a-b]oxirene-7-carboxylate

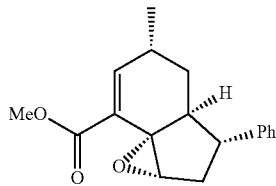 [SMILES: COC(=O)C1=C[C@H](C)C[C@H]2[C@H](c3ccccc3)C[C@@H]3O[C@@]132]

Obtained in quantitative yield as a 1:0.4:0.2 diastereomeric mixture.
Major Diastereomer
$^1$H NMR 7.30 (3H, m), 7.22 (2H, m), 6.95 (1H, dd, J=5.3 and 1.4 Hz), 4.11 (1H, s), 3.74 (3H, s), 3.45 (1H, dt, J=11.2 and 7.9 Hz), 2.61 (1H, m), 2.50 (1H, m), 2.36 (1H, dd, J=14.0 and 7.5 Hz), 1.85 (1H, m), 1.41 (1H, dt, J=13.8 and 5.8), 1.06 (3H, d, J=7.2 Hz), 0.95 (1H, m)
$^{13}$C NMR (CDCl$_3$) δ 165.7, 154.5, 149.8, 142.1, 128.7, 128.5, 126.5, 65.8, 63.4, 51.9, 41.0, 37.7, 30.7, 30.0, 29.3, 18.8
HRMS calcd for C$_{18}$H$_{21}$O$_3$ [M+1]: 285.1491. found: 285.1480.

Example 13

Methyl 1a,2,3,3a4,5-hexahydro-3,3,5-trimethyl-indeno[1,7a-b]oxirene-7-carboxylate

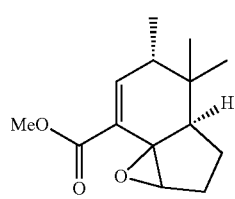 [SMILES: COC(=O)C1=C[C@H](C)C(C)(C)[C@H]2CCC3OC132]

Obtained as a 2:1 diastereomeric mixture in form of a clear oil in 83% yield.

Major Diastereoisomer
$^1$H NMR (CDCl$_3$) δ 7.22 (1H, s, J=5.2 Hz), 4.24 (1H, s), 3.73 (3H, s), 2.36 (1H, m), 2.08 (1H, m), 1.95 (1H, dd, J=11.3 and 7.2 Hz), 1.72 (1H, m), 1.62 (1H, m), 1.30 (1H, m), 1.04 (3H, d, J=7.4 Hz), 0.99 (3H, s), 0.93 (3H, s)
$^{13}$C NMR (CDCl$_3$) δ 165.7, 154.1, 125.7, 62.5, 61.0, 51.8, 44.1, 43.8, 34.0, 28.3, 25.1, 23.5, 17.8, 14.9
Minor Diastereoisomer
$^1$H NMR (CDCl$_3$) δ 7.03 (1H, d, J=5.8 Hz), 4.14 (1H, s), 3.72 (3H, s), 2.26 (1H, dd, J=8.8 and 2.2 Hz), 2.08 (2H, m), 1.72 (1H, m), 1.62 (1H, m), 1.30 (1H, m), 1.07 (3H, d, J=7.2 Hz), 0.93 (3H, s), 0.82 (3H, s)
$^{13}$C NMR (CDCl$_3$) δ 165.6, 149.6, 126.5, 65.6, 65.7, 51.8, 43.0, 42.8, 36.0, 28.3, 26.2, 23.7, 21.2, 15.4,
HRMS calcd for C$_{14}$H$_{21}$O$_3$ [M+1]: 237.1491. found: 237.1488.

Example 14

Methyl 1a,2,3,3a,4,5-hexahydro-2-benzyl-indeno[1,7a-b]oxirene-7-carboxylate

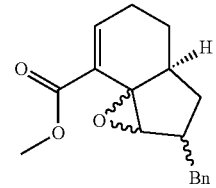

Obtained after flash chromatography (heptane: EtOAc, 10:1) as a yellow oil, as a 1:1 diastereomeric mixture, in 72% yield.
Isomer
$^1$H NMR (CDCl$_3$) δ 7.34 (1H, m), 7.29 (2H, m), 7.20 (3H, m), 4.32, (1H, s), 3.72 (3H, s), 2.72 (1H, m), 2.52 (1H, m), 2.35 (2H, m), 1.85 (2H, m), 1.61 (1H, m), 1.57 (1H, m), 1.27 (1H, m), 0.88 (1H, m)
$^{13}$C NMR (CDCl$_3$) δ 149.4, 140.0, 129.0, 128.4, 126.1, 66.8, 62.9, 51.6, 42.6, 38.6, 37.1, 26.4, 30.0, 28.6, 27.5, 23.3
Isomer
$^1$H NMR (CDCl$_3$) δ 7.34 (1H, m), 7.29 (2H, m), 7.20 (3H, m), 4.32, (1H, s), 3.72 (3H, s), 2.88 (1H, m), 2.58 (2H, m), 2.26 (2H, m), 1.92 (2H, m), 1.40 (1H, m), 1.21 (1H, m), 0.91 (1H, m)
$^{13}$C NMR (CDCl$_3$) δ 149.4, 140.0, 129.0, 128.4, 126.0, 68.8, 66.8, 51.6, 41.3, 38.6, 37.3, 36.5, 28.6, 27.7, 26.4, 23.3
HRMS calc δ for C$_{18}$H$_{21}$O$_3$ [M+1]: 285.1491. found: 285.1491.

Scheme 14

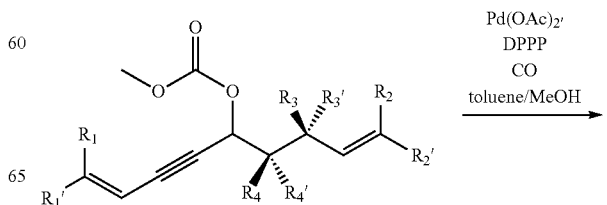

-continued

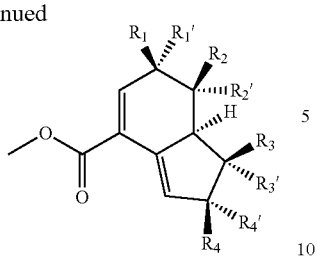

General procedure for the intramolecular vinylallene Diels-Alder reaction (scheme 14).

Pd(OAc)$_2$ (0.2 eq) and DPPP (0.2 eq) were weighed into a predried autoclave vessel and suspended in toluene. A solution of the carbonate (1.0 eq), in MeOH/toluene 2:1, was added after which CO was bubbled though the solution. The autoclave was sealed and the atmosphere replaced by repeatedly filling with 1-2 bar of CO and releasing the pressure. The mixture was stirred until the reaction completes (typically over night) after which it was diluted with EtOAc and filtered through a plug of Celite. The filtrate was concentrated and the crude product purified through column chromatography on silica gel (heptane/Et$_2$O 1000:1).

Methyl 6-methyl-2-phenyl-2,6,7,7a-tetrahydro-1H-indene-4-carboxylate

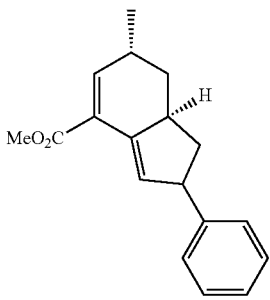 [SMILES: COC(=O)C1=C[C@H](C)C[C@H]2CC(c3ccccc3)C=C12]

Obtained after flash chromatography as a diastereomeric mixture in the form of a clear oil in 46% yield.

Major Isomer Trans:

$^1$H NMR (CDCl$_3$) δ 7.31 (2H, m), 7.22 (3H, m), 6.97 (1H, d, J=5.4 Hz), 6.34 (1H, m), 4.01 (1H, m), 3.79 (3H, s), 2.87 (1H, m), 2.67 (1H, m), 2.62 (1H, dt, J=12.6 and 7.2 Hz), 1.99 (1H, dt, J=12.7 and 9.5 Hz), 1.88 (1H, m), 1.55 (1H, m), 1.37 (1H, t, J=10.1 Hz), 1.16 (3H, d, J=7.3 Hz)

$^{13}$C NMR (CDCl$_3$) δ 167.2, 146.5, 146.1, 138.2, 131.2, 129.0, 128.6, 127.6, 126.3, 51.8, 51.3, 42.5, 39.5, 35.8, 31.3, 20.0

Minor Isomer Cis:

$^1$H NMR (CDCl$_3$) δ 7.31 (2H, m), 7.22 (3H, m), 6.97 (1H, d, J=5.4 Hz), 6.42 (1H, t, J=2.5 Hz), 4.01 (1H, m), 3.80 (3H,$), 3.00 (1H, m), 2.67 (1H, m), 2.62 (1H, dt, J=12.6 and 7.2 Hz), 2.15 (1H, ddd, J=12.6 and 7.2 Hz), 1.83 (1H, m), 1.55 (1H, m), 1.37 (1H, t, J=10.1 Hz), 1.16 (3H, d, J=7.3 Hz)

$^{13}$C NMR (CDCl$_3$) δ 167.2, 146.7, 145.8, 138.1, 130.2, 129.0, 128.6, 127.4, 126.3, 51.3, 50.4, 40.1, 38.2, 36.0, 31.5, 20.0

HRMS calcd for C$_{18}$H$_{19}$O$_2$ [M−1]: 267.1385. found: 267.1375.

Methyl 2-benzyl-6-methyl-2,6,7,7a-tetrahydro-1H-indene-4-carboxylate

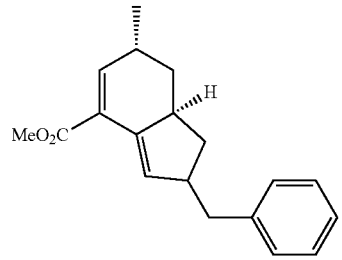 [SMILES: COC(=O)C1=C[C@H](C)C[C@H]2CC(Cc3ccccc3)C=C12]

Obtained after flash chromatography as a diastereomeric mixture in the form of a clear oil in 60% yield.

Major Isomer (Cis-Cis)

$^1$H NMR (CDCl$_3$) δ 7.28 (2H, m), 7.21 (3H, m), 6.88 (1H, d, J=5.3 Hz), 6.23 (1H, m), 3.78 (3H, s), 3.01 (1H, m), 2.82 (1H, m), 2.75 (1H, dd, J=13.5 and 6.7 Hz), 2.60 (1H, m), 2.59 (1H, m), 1.92 (1H, dd, J=12.7 and 7.0 Hz), 1.76 (1H, dt, J=12.9 and 4.4 Hz), 1.51 (1H, dt, J=12.8 and 9.0 Hz) 1.40 (1H, m), 1.10 (3H, d, J=7.5 Hz)

$^{13}$C NMR (CDCl$_3$) δ 167.0, 145.8, 141.4, 137.0, 131.2, 129.0, 128.1, 126.1, 125.7, 51.5, 46.5, 40.8, 37.1, 35.8, 35.7, 31.1, 19.8

Minor Isomer (Cis-Trans)

$^1$H NMR (CDCl$_3$) δ 7.28 (2H, m), 7.21 (3H, m), 6.88 (1H, d, J=5.3 Hz), 6.28 (1H, m), 3.77 (3H, s), 3.09 (1H, m), 2.85 (1H, dd, J=13.4 and 7.0 Hz), 2.74 (1H, m), 2.64 (1H, m), 2.60 (1H, m), 2.21 (1H, dt, J=12.1 and 6.8 Hz), 1.77 (1H, m), 1.44 (2H, m), 1.10 (3H, d, J=7.5 Hz), 1.05 (1H, m)

$^{13}$C NMR (CDCl$_3$) δ 167.0, 145.8, 141.2, 137.1, 131.3, 128.8, 128.2, 126.0, 125.8, 51.5, 47.2, 42.3, 38.9, 38.6, 35.7, 31.0, 19.8

HRMS calcd for C$_{19}$H$_{21}$O$_2$ [M−1]: 281.1542. found: 281.1529.

Methyl 2,2,6-trimethyl-2,6,7,7a-tetrahydro-1H-indene-4-carboxylate

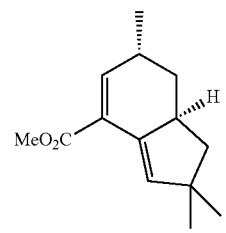

Obtained after flash chromatography as a colourless oil in 73% yield.

$^1$H NMR (CDCl$_3$) δ 6.86 (1H, d, J=5.4 Hz), 6.09 (1H, d, J=2.1 Hz), 3.77 (3H, s), 2.90 (1H, m), 2.59 (1H, m), 1.92 (1H, dd, J=12.0 and 6.7 Hz), 1.75 (1H, ddd, J=12.7, 4.6 and 1 Hz), 1.42 (1H, dt, J=12.9 and 5.9 Hz), 1.26 (1H, dd, J=11.7 and 9.7 Hz) 1.15 (3H, s), 1.12 (3H, d, J=7.3 Hz), 1.07 (3H, s)

$^{13}$C NMR (CDCl$_3$) δ 167.3, 145.9, 138.1, 134.4, 126.3, 51.7, 46.8, 44.7, 38.2, 35.9, 31.2, 29.7, 27.2, 20.0

HRMS calcd for C$_{14}$H$_{19}$O$_2$ [M−1]: 219.1385. found: 219.1386.

Methyl 6-methyl-1-phenyl-2,6,7,7a-tetrahydro-1H-indene-4-carboxylates

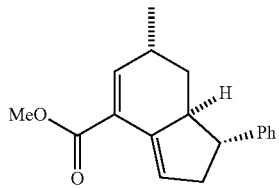 [SMILES: COC(=O)C1=C[C@H](C)C[C@@H]2C1=CC[C@H]2c1ccccc1]

Obtained as a 3:1 diastereomeric mixture as a clear oil in 35% yield after flash chromatography.
Major Isomer
$^1$H NMR (CDCl$_3$) δ 7.33 (3H, m), 7.24 (2H, m), 6.90, (1H, d, J=5.4 Hz), 6.34 (1H, dd, J=4.9 and 2.4 Hz), 3.82 (3H, s), 2.98 (1H, td, J=8.4 and 10.0 Hz), 2.87 (2H, m), 2.65 (1H, m), 2.65 (1H, m), 1.80 (1H, ddd, J=12.8, 4.4 and 1.0 Hz), 1.51 (1H, td, J=12.8 and 5.8 Hz), 1.05 (3H, d, J=7.3)
$^{13}$C NMR (CDCl$_3$) δ 167.3, 145.8, 144.3, 136.3, 128.7, 128.4, 128.2, 127.9, 127.3, 52.8, 51.9, 46.8, 41.4, 34.4, 31.3, 20.1
Minor Isomer
$^1$H NMR (CDCl$_3$) δ 7.33 (3H, m), 7.15 (2H, m), 6.84 (1H, d, J=5.5 Hz), 6.53 (1H, dd, J=5.2 and 2.6 Hz), 3.81 (3H, s), 3.55 (1H, t, J=7.8 Hz), 3.16 (1H, m), 3.09 (2H, m), 2.75 (1H, m), 2.75 (1H, m), 2.49 (1H, m), 1.07 (3H, d, J=7.3 Hz)
$^{13}$C NMR (CDCl$_3$) δ 167.3, 145.6, 144.5, 135.6, 126.5, 126.5, 126.3, 126.2, 126.0, 52.8, 51.8, 45.7, 43.4, 41.0, 29.3, 19.9

HRMS calcd for C$_{18}$H$_{21}$O$_2$ [M+1]: 269.1542. found: 269.1548.

Methyl 4,4,6-trimethyl-2,6,7,7a-tetrahydro-1H-indene-4-carboxylate

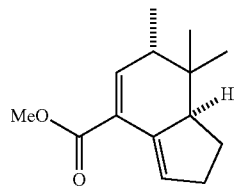 [SMILES: COC(=O)C1=C[C@H](C)C(C)(C)[C@H]2CCC=C12]

Obtained as clear oil in 28% yield after flash chromatography using heptane/EtOAc (100:1) as eluent.
$^1$H NMR (CDCl$_3$) δ 6.84 (1H, d, J=5.8 Hz), 6.35 (1H, dd, J=5.1 and 2.5 Hz), 3.78 (3H, s), 2.69 (1H, m), 2.44 (2H, m), 2.16 (1H, m), 1.86 (1H, m), 1.55 (1H, m), 1.00 (3H, d, J=7.3 Hz), 0.90 (3H, s), 0.70 (3H, s)
$^{13}$C NMR (CDCl$_3$) δ 167.2, 145.7, 136.3, 128.8, 125.6, 51.7, 48.5, 44.0, 34.0, 32.5, 25.1, 23.9, 22.7, 15.7

HRMS calcd for C$_{14}$H$_{19}$O$_2$ [M−1]: 269.1542. found: 269.1548.

Methyl 2-benzyl-2,6,7,7a-tetrahydro-1H-indene-4-carboxylates

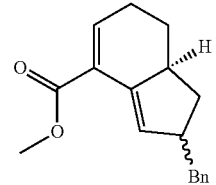 [SMILES: COC(=O)C1=CCC[C@H]2CC(Cc3ccccc3)C=C12]

Obtained after flash chromatography (heptane: EtOAc, 10:1) as a 2:1 diastereomeric mixture of yellow oil with 56% yield.
Major Isomer
$^1$H NMR (CDCl$_3$) δ 7.28 (3H, m), 7.19 (2H, m), 6.92, (1H, m), 6.21 (1H, m), 3.76 (3H, s), 3.07 (1H, m), 2.84 (2H, m), 2.61 (1H, m), 2.37 (1H, m), 2.21 (1H, t, J=6.9 Hz), 1.94 (1H, m), 1.54 (1H, m), 1.29 (1H, m), 1.08 (1H, t, J=9.9 Hz)
$^{13}$C NMR (CDCl$_3$) δ 166.9, 141.4, 130.9, 129.2, 129.0, 128.9, 128.2, 126.4, 125.7, 51.6, 46.4, 42.2, 40.8, 38.6, 35.8, 29.2, 27.1
Minor Isomer
$^1$H NMR (CDCl$_3$) δ 7.28 (3H, m), 7.19 (2H, m), 6.92, (1H, m), 6.26 (1H, m), 3.77 (3H, s), 2.99 (1H, m), 2.73 (2H, m), 2.55 (1H, m), 2.37 (1H, m), 2.21 (1H, t, J=6.9 Hz), 1.98 (1H, m), 1.52 (1H, m), 1.24 (1H, m), 1.05 (1H, t, J=9.9 Hz)
$^{13}$C NMR (CDCl$_3$) δ 166.9, 141.4, 130.9, 129.2, 129.0, 128.9, 128.2, 126.4, 125.8, 51.5, 46.4, 42.2, 40.8, 38.6, 35.8, 29.2, 26.9

HRMS calc for C$_{18}$H$_{21}$O$_2$ [M+1]: 269.1542. found 269.1540.

Scheme 15

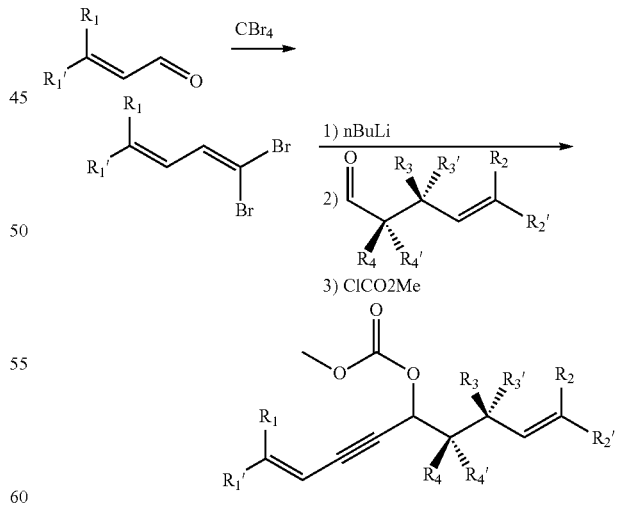

General procedure for the synthesis of alkyne carbonates (scheme 15)

CBr$_4$ (2.0 eq) and PPh$_3$ (4.0 eq) were added to a solution of crotonaldehyde (1.0 eq) in CH$_2$Cl$_2$ at 0° C. The mixture was stirred for 30 min in the dark after which it was diluted with hexanes and filtered through Celite. The filtrate was carefully concentrated and dissolved in dry THF (150 mL). The solution was cooled to −78° C. under nitrogen. n-BuLi (1.6 M in hexanes, 1.0 eq) was added dropwise after which the solution was stirred for 1 hour. Additional n-BuLi (1.6 M in hexanes, 1.0 eq) was added dropwise, upon complete addition the mixture was stirred at room temperature for 1 hour after which it was cooled to −78° C. The corresponding 4-pentenal (1.1 eq) was added dropwise over 15 min, the reaction mixture was stirred for 20 min after which methyl chloroformate (1.1 eq) was added dropwise. Upon completion the reaction was quenched with saturated $NH_4Cl(aq)$, the mixture was diluted with EtOAc and the phases were separated, the aqueous phase was extracted with additional EtOAc. The combined organic phases were dried over $Na_2SO_4$ and concentrated. The crude product was purified through column chromatography on silica gel (heptane/EtOAc 1000:1).

Biological Examples

Example 15

STAT3 inhibition

HeLa cells ($4\times10^4$/ml) were transiently transfected with a luciferase reporter plasmid (4×M67 pTATA TK-Luc) driven by artificial promoter containing 4 repeated M67 binding sites in tandem for the STAT-3 transcription factor. The transfections were performed for 24 h using Roti-Fect reagent (Carl Roth, Karlsruhe, Germany) according to the manufacturer's recommendations. After incubation with different concentrations of the extracts for 30 min the transfected cells were stimulated for 8 h with γ-Interferon. Then, the cells were lysed in 25 mM Tris-phosphate pH 7.8, 8 mM $MgCl_2$, 1 mM DTT, 1% Triton X-100, and 7% glycerol. Luciferase activity was measured as described for 5.1 cells.

γ-Interferon induces an average of 5-6 fold induction of the luciferase activity compared to non stimulated cells and this represent the index of transactivation that is represented in our experiment as the maximum levels of γ-Interferon-induced STAT-3 activation (100%). Results below represent the IC50 for each compound in this assay. The IC50 means the concentration of each compound that reduces luciferase activity by 50% and it was calculated by GraphPad software.

STAT3 Inhibition

| Compound | Anti STAT3 $IC_{50}$ (uM) |
|---|---|
| (−)-Galiellalactone | 7.70 |
| Example 1 | 2.10 |
| Example 2 | 1.18 |
| Example 3 | 2.87 |
| Example 7 | 1.83 |
| Example 8 | 0.75 |
| Example 9 | 2.01 |
| Example 10 | 2.98 |
| Example 11 | 2.49 |

Example 16

Cancer Cell Proliferation

The human prostate cancer cell lines DU145, LNCaP (from the American Type culture Collection, ATCC) and long-term interleukin-6 (IL-6) stimulated LNCaP cells (LNCaP-IL6 cells) (Hobisch, Ramoner et al. 2001) were used. The cells were cultured in RPMI 1640 medium supplemented with 10% FBS and 1% penicillin-streptomycin. All cells were incubated at 37° C. in a humidified atmosphere of 95% O2 and 5% CO2.

WST-1 proliferation assay was performed to study the effects of the test items on the proliferation and viability of cultured prostate cancer cells. LNCaP and DU145 cells were cultured in 96-well plates at the density of 2 000 cells/well in 200 μl of medium. Cells were allowed to set for 24 h. The cells were treated with 0, 2.5, 5 or 10 μM of the specific substance for 24 h and 48 h. Samples were made in triplicate. 20 μl WST-1 solution (Roche Applied Science, Mannheim, Germany) was added per well and incubated at 37° C. for 4 h. The absorbance of each well was measured using a scanning multiwell spectrophotometer, ELISA reader at a wavelength of 450 nm and reference wavelength of 690 nm. The results are presented as percent of untreated control cells or the absorbance value.

| | | % Proliferation (vs control) | | | |
|---|---|---|---|---|---|
| Compound | conc (uM) | 24 h LNCaP-IL6 | 48 h LNCaP-IL6 | 24 h DU145 | 48 h Du145 |
| (−)-Galiellalactone | 2.5 | 90.91 | 96.78 | 84.24 | 76.36 |
| | 5 | 68.76 | 68.76 | 63.19 | 38.51 |
| | 10 | 77.11 | 23.22 | 48.44 | 22.24 |
| Example 1 | 2.5 | 65.41 | 52.42 | 80.19 | 67.45 |
| | 5 | 68.95 | 26.28 | 68.82 | 35.62 |
| | 10 | 69.23 | 16.19 | 54.07 | 22.77 |
| Example 2 | 2.5 | 81.79 | 79.56 | 90.64 | 68.04 |
| | 5 | 81.21 | 57.14 | 68.55 | 34.07 |
| | 10 | 70.45 | 20.19 | 63.86 | 30.26 |
| Example 3 | 2.5 | 57.10 | 27.82 | 56.33 | 31.10 |
| | 5 | 59.00 | 18.15 | 52.11 | 18.38 |
| | 10 | 53.01 | 12.49 | 44.48 | 14.45 |
| Example 7 | 2.5 | 81.79 | 82.60 | 90.64 | 95.09 |
| | 5 | 81.21 | 85.26 | 68.55 | 75.05 |
| | 10 | 70.45 | 71.27 | 63.86 | 76.58 |
| Example 8 | 2.5 | 69.23 | 48.79 | 80.94 | 63.59 |
| | 5 | 58.97 | 20.28 | 58.19 | 27.29 |
| | 10 | 52.67 | 18.81 | 48.49 | 19.98 |
| Example 9 | 2.5 | 92.78 | 104.12 | 96.36 | 93.96 |
| | 5 | 90.02 | 108.49 | 88.29 | 85.24 |
| | 10 | 96.73 | 96.48 | 75.01 | 55.43 |
| Example 10 | 2.5 | 81.18 | 74.81 | 86.82 | 88.02 |
| | 5 | 92.69 | 80.02 | 98.85 | 92.54 |
| | 10 | 76.05 | 23.18 | 66.76 | 28.27 |
| Example 11 | 2.5 | 93.47 | 78.36 | 93.88 | 85.06 |
| | 5 | 89.35 | 71.85 | 80.42 | 67.77 |
| | 10 | 79.82 | 31.62 | 72.14 | 45.51 |

Example 17

Cancer Cell Proliferation

The human prostate cancer cell line DU145 was used. The cells were cultured in RPMI 1640 medium supplemented with 10% FBS and 1% penicillin-streptomycin. All cells were incubated at 37° C. in a humidified atmosphere of 95% O2 and 5% CO2.

WST-1 proliferation assay was performed to study the effects of the test items on the proliferation and viability of cultured prostate cancer cells. DU145 cells were cultured in 96-well plates at the density of 2 000 cells/well in 200 μl of medium. Cells were allowed to set for 24 h and 48 h. The cells were treated with 0.5, 1.0, 2.5, 5.0, 10, and 50 μM of the specific substance for 24 h and 48 h. Samples were made in triplicate. 20 μl WST-1 solution (Roche Applied Science, Mannheim, Germany) was added per well and incubated at 37° C. for 4 h. The absorbance of each well was measured using a scanning multiwell spectrophotometer, ELISA reader at a wavelength of 450 nm and reference wavelength of 690 nm. The results are presented as percent of untreated control cells or the absorbance value.

| Proliferation (vs control) Du145 (%) | | | |
|---|---|---|---|
| Compound | Conc. (μM) | 24 h | 48 h |
| Example 4 | 0.5 | 125.24 | 161.90 |
| | 1.0 | 76.74 | 106.97 |
| | 2.5 | 86.48 | 106.23 |
| | 5.0 | 91.39 | 73.13 |
| | 10.0 | 45.29 | 59.35 |
| | 25.0 | 22.17 | 21.83 |
| | 50.0 | 18.31 | 11.34 |
| Example 5 | 0.5 | 105.62 | 98.92 |
| | 1.0 | 101.40 | 93.59 |
| | 2.5 | 72.14 | 53.09 |
| | 5.0 | 54.75 | 35.53 |
| | 10.0 | 39.62 | 29.96 |
| | 25.0 | 28.13 | 13.26 |
| | 50.0 | 14.36 | 8.51 |
| Example 6 | 0.5 | 110.14 | 121.11 |
| | 1.0 | 98.76 | 120.77 |
| | 2.5 | 104.13 | 101.61 |
| | 5.0 | 81.25 | 78.86 |
| | 10.0 | 43.88 | 42.70 |
| | 25.0 | 45.01 | 23.80 |
| | 50.0 | 23.59 | 9.88 |

Example 18

NF-κB Inhibition

The potency of (−)-Galiellalactone and compound examples of the invention in inhibiting NF-κB-dependent transcriptional activity was assayed in a Jurkat-LTR-Luc cell line. This cellular model have been widely used for the screening of natural and synthetic NF-κB inhibitors (Appendino et al, J Nat Prod. 2007, 70(4), 608-612; J Nat Prod. 2006, 69(7), 1101-1104; Marquez et al, Antiviral Res. 2005, 66(2-3), 137-145) Jurkat 5.1 cells were preincubated for 30 min with increasing concentrations of the compounds dissolved in DMSO followed by stimulation with TNF-α (2 ng/ml) for 6 h. Cells were washed twice in PBS and lysed in 25 mM Tris-phosphate, pH 7.8, 8 mM $MgCl_2$, 1 mM DTT, 1% Triton X-100, and 7% glycerol for 15 min at room temperature. Then the lysates were spun down and the supernatant was used to measure luciferase activity using an Autolumat LB 9510 (Berthold Technologies). Protein concentration was determined by the Bradford method (Bio-Rad, Richmond, Calif.). Results below represent the 1050 for each compound in this assay.

| Compound | IC50 anti-NF-κB |
|---|---|
| (−)-Galiellalactone | 5.5 μM |
| Example 1 | 2.66 μM |
| Example 2 | 0.33 μM |
| Example 3 | 1.26 μM |

The invention claimed is:

1. A compound according to formula (I) or (II),

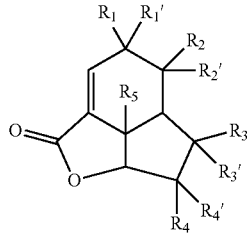

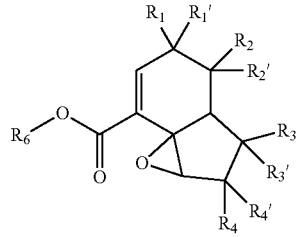

wherein $R_1$ and $R_1'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneS02C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl;

$R_2$ and $R_2'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl;

$R_3$ and $R_3'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl;

$R_4$ and $R_4'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneNHaryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl;

$R_5$ is selected from the group consisting of OC0-5 alkyl, OC1-5 fluoroalkyl, OC(O)C1-5 alkyl, 0C2-3 alkyleneN(C0-5 alkyl)2 in which the C0-5 alkyl may be the same or different, NHC0-5 alkyl, N(C1-5 alkyl)2 in which the C1-5 alkyl may be the same or different, N(C0-5 alkyl)C(O)C1-5 alkyl, NHaryl, NHheteroaryl, a 3- to 8-membered non-aromatic heterocycle which is connected via a substitutable heteroatom of said non-aromatic heterocycle, SC0-5 alkyl, S(O)C0-5 alkyl, SO2C0-5 alkyl, and N(C0-C3 alkyl)SO2C1-C5 alkyl;

$R_6$ is selected from the group consisting of H, C1-5 alkyl, C1-5 fluoroalkyl, and a C3-8 non-aromatic carbocycle; and at least one of $R_2$, $R_2'$, $R_3$, $R_3'$, $R_4$ and $R_4'$ is comprising a carbon atom, an oxygen atom or a nitrogen atom;

said heteroaryl is a 5-membered heteroaryl, or a 6-membered heteroaryl; and as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two heteroatoms, or the corresponding tautomeric form resulting from a keto-enol tautomerization.

2. The compound according to claim 1, wherein the relative or absolute stereochemistry of $R_1$, $R_1'$, $R_2$, $R_2'$, $R_3$, $R_3'$, $R_4$, $R_4'$, R5 and the hydrogen atoms at positions 5a and 7a of said compound of formula (I) is

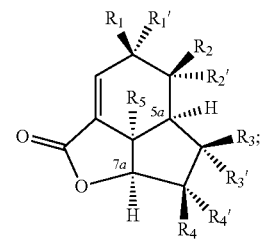

or the relative or absolute stereochemistry of $R_1$, $R_1'$, $R_2$, $R_2'$, $R_3$, $R_3'$, $R_4$, $R_4'$, the hydrogen atom at positions 5a and the oxygen atom at position 7a and 7b of said compound of formula (II) is

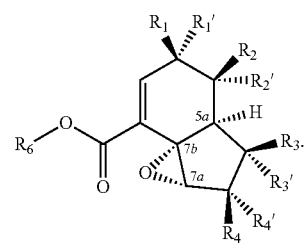

3. The compound according to claim 1, wherein $R_1$, $R_1'$, $R_2$, $R_2'$, $R_3$, $R_3'$, $R_4$ and $R_4'$ are independently selected from the group consisting of H, C1-5 alkyl, aryl, CH2aryl, heteroaryl and CH2heteroaryl.

4. The compound according to claim 3, wherein at least one of $R_2$, $R_2'$, $R_3$, $R_3'$, $R_4$ and $R_4'$ is selected from the group consisting of C1-5 alkyl, aryl, CH2aryl, heteroaryl and CH2heteroaryl.

5. The compound according to claim 4, wherein at least one of $R_3$, $R_3'$, $R_4$ and $R_4'$ is selected from the group consisting of C1-5 alkyl, aryl, CH2aryl, heteroaryl and CH2heteroaryl.

6. The compound according to claim 5, wherein at least one of $R_4$ and $R_4'$ is selected from the group consisting of C1-5 alkyl, aryl, CH2aryl, heteroaryl and CH2heteroaryl.

7. The compound according to claim 1, wherein $R_1$ and $R_1'$ are independently selected from the group consisting of H and methyl.

8. A compound according to formula (II)

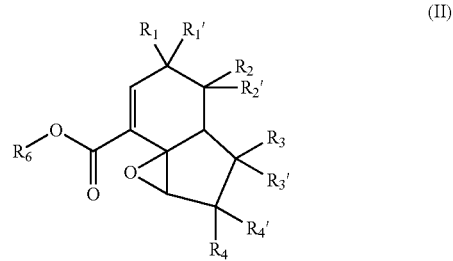

wherein $R_6$ is C1-5 alkyl or
a compound according to formula (I)

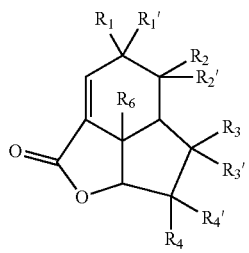

wherein $R_5$ is OH, OC1-5, OC1-5 fluoroalkyl, or OC(O)C1-5 alkyl;
wherein
$R_1$ and $R_1'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-05 alkyl, and N(C0-C5 alkyl)SO2C1-5 fluoroalkyl;
$R_2$ and $R_2'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl;
$R_3$ and $R_3'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl;
$R_4$ and $R_4'$ are independently selected from the group consisting of H, C1-5 alkyl, C1-5 fluoroalkyl, C3-8 non-aromatic carbocycle C0-5 alkyleneOC0-5 alkyl, C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl; and
at least one of $R_2$, $R_2'$, $R_3$, $R_3'$, $R_4$ and $R_4'$ is comprising a carbon atom, an oxygen atom or a nitrogen atom;
said heteroaryl is a 5-membered heteroaryl, or a 6-membered heteroaryl; and
as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two heteroatoms, or the corresponding tautomeric form resulting from a keto-enol tautomerization.

9. A compound according to formula (I) or (II),

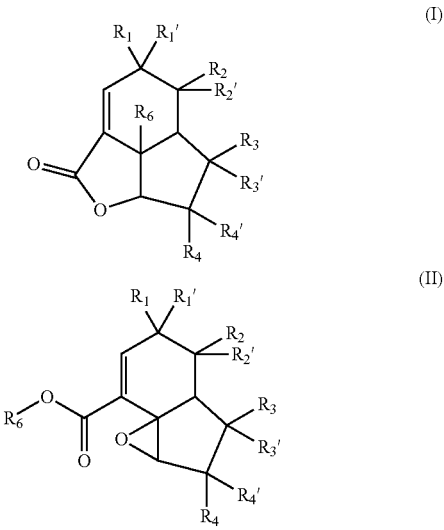

wherein $R_1$, $R_1'$, $R_2$, $R_2'$ $R_3$, $R_3'$, $R_4$ and $R_4'$ are independently selected from the group consisting of H, C1-5 alkyl, aryl, CH2aryl, heteroaryl and CH2heteroaryl;

47

$R_5$, if present, is OH, NHC0-5 alkyl, NHaryl or NHheteroaryl; and $R_6$, if present, is C1-5 alkyl; and at least one of $R_2$, $R_2'$, $R_3$, $R_3'$ $R_4$ and $R_4'$ is comprising a carbon atom, an oxygen atom, or a nitrogen atom;

said heteroaryl is a 5-membered heteroaryl or a 6-membered heteroaryl; and as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two heteroatoms, or the corresponding tautomeric form resulting from a keto-enol tautomerization.

10. A compound according to formula (I)

(I)

wherein $R_1$ and $R_1'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different C0-3 alkyleneN(C0-5 alkyl)C(O)C1-5 alkyl C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N C4-5 alkylene C0-3 alkyleneC(O)OC0-5 alkyl a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O)C1-C5 fluoroalkyl, N(C0-C3 alkyl)SO2C1-C5 alkyl, and N(C0-C5 alkyl)SO2C1-5 fluoroalkyl;

$R_2$ and $R_2'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different C0-3 alkyleneN(C0-5 alkyl C(O)C1-5 alkyl C0-3 alkyleneN-Haryl, C0-3 alkyleneNHheteroaryl, C0-3 alkyleneC0 NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O) C1-C5 fluoroalkyl, N(C0-C3 alkyl)SO2C1-05 alkyl, and N(C0-C5 alkyl)SO2C1-5 fluoroalkyl;

48

$R_3$ and $R_3'$ are independently selected from the group consisting of H, C1-5 alkyl, C1-5 fluoroalkyl, C3-8 non-aromatic carbocycle, C0-5 alkyleneOC0-5 alkyl, C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O) C1-C5 fluoroalkyl, N(C0-C3 alkyl)SO2C1-C5 alkyl, and N(C0-C5 alkyl)SO2C1-5 fluoroalkyl;

$R_4$ and $R_4'$ are independently selected from the group consisting of H, C1-5 alkyl, C1-5 fluoroalkyl, C3-8 non-aromatic carbocycle, C0-5 alkyleneOC0-5 alkyl)C0-3 alkyleneOC1-5 fluoroalkyl, C0-3 alkyleneOC(O)C1-5 alkyl, 0C2-3 alkyleneN(C0-5 alkyl)2 in which the C0-5 alkyl may be the same or different, C0-3 alkyleneNHC0-5 alkyl, C0-3 alkyleneN(C1-5 alkyl)2 in which the C1-5 alkyl may be the same or different, C0-3 alkyleneN(C0-5 alkyl C(O)C1-5 alkyl, C0-3 alkyleneN-Haryl, C0-3 alkyleneNHheteroaryl, C0-3 alkyleneC(O)NHC0-5 alkyl, C0-3 alkyleneC(O)N(C1-5 alkyl)2 in which the C1-5 alkyl may be the same or different, C0-3 alkyleneC(O)N(C4-5 alkylene C0-3 alkyleneC(O)) C0-5 alkyl a 3- to 8-membered non-aromatic heterocycle, C0-3 alkylene aryl, C0-3 alkylene heteroaryl, halo, C0-1 alkylene cyano, SC0-5 alkyl, C0-3 alkyleneSO2C0-5 alkyl, nitro, C(O)C0-C5 alkyl, C(O) C1-05 fluoroalkyl, N(C0-C3 alkyl)SO2C1-C5 alkyl, and N(C0-C5 alkyl)SO2C1-5 fluoroalkyl;

R5 is OH;

at least one of $R_2$, $R_2'$, $R_3$, $R_3'$, $R_4$ and $R_4'$ is comprising a carbon atom, an oxygen atom, or a nitrogen atom;

said heteroaryl is a 5-membered heteroaryl or a 6-membered heteroaryl; and as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two heteroatoms, or the corresponding tautomeric form resulting from a keto-enol tautomerization.

11. The compound according to claim 1, wherein said compound is a compound according to formula (II)

(II)

and R6 is C1-5 alkyl.

12. A compound selected from the group consisting of

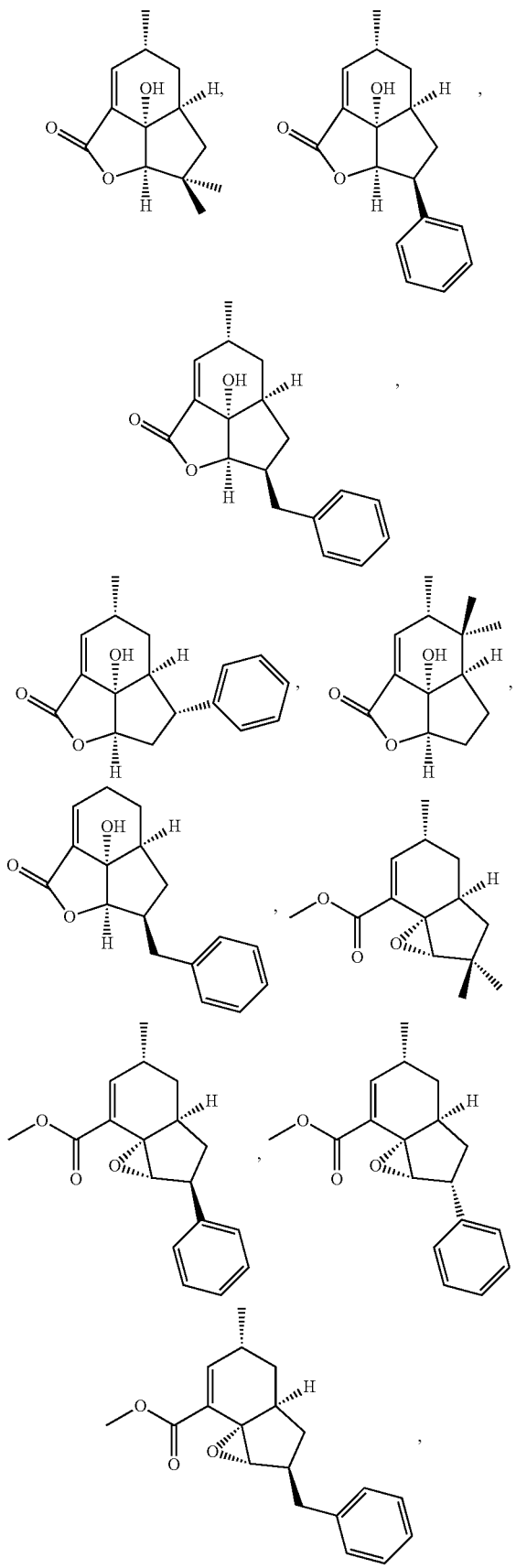

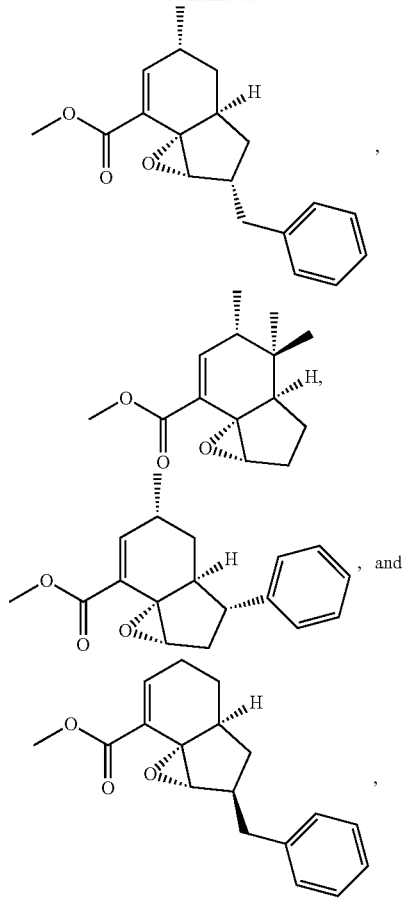

and wherein the indicated stereochemistry is relative stereochemistry; and as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two heteroatoms, or the corresponding tautomeric form resulting from a keto-enol tautomerization.

13. A pharmaceutical composition comprising a compound according to claim 1 and at least one pharmaceutically acceptable carrier or excipient.

14. The pharmaceutical composition according to claim 13, wherein said composition further comprises at least one more therapeutic agent.

15. The pharmaceutical composition according to claim 14, wherein said at least one more therapeutic agents is selected from the group consisting of Abraxane, Aldesleukin, Alemtuzumab, Aminolevulinic Acid, Anastrozole, Aprepitant, Arsenic Trioxide, Azacitidine, Bendamustine Hydrochloride, Bevacizumab, Bexarotene, Bortezomib, Bleomycin, Cabazitaxel, Capecitabine, Carboplatin, Cetuximab, Cisplatin, Clofarabine, Cyclophosphamide, Cytarabine, Dacarbazine, Dasatinib, Daunorubicin Hydrochloride, Decitabine, Degarelix, Denileukin Diftitox, Dexrazoxane Hydrochloride, Docetaxel, Doxorubicin Hydrochloride, Doxorubicin Hydrochloride Liposome, Eltrombopag Olamine, Epirubicin Hydrochloride, Erlotinib Hydrochloride, Etoposide, Etoposide Phosphate, Everolimus, Exemestane, Filgrastim, Fludarabine Phosphate, Fluorouracil, Fulvestrant, Gefitinib, Gemcitabine Hydrochloride, Ibritumomab Tiuxetan, Imatinib Mesylate, Imiquimod, Irinotecan Hydrochloride, Ixabepilone, Lapatinib Ditosylate, Lenalidomide, Letrozole, Leucovorin Calcium, Leuprolide Acetate, Liposomal Cytarabine, Methotrexate, Nelarabine, Nilotinib, Ofatumumab, Oxaliplatin, Paclitaxel, Palifetmin, Palonosetron Hydrochloride, Panitumumab, Pazopanib Hydrochloride, Pegaspargase, Pemetrexed Disodium, Plerixafor, Pralatrexate, Raloxifene Hydrochloride, Rasburicase, Recombinant HPV Bivalent Vaccine, Recombinant HPV Quadrivalent Vaccine, Rituximab, Romidepsin, Romiplostim, Sipuleucel-T, Sorafenib Tosylate, Sunitinib Malate, Talc, Tamoxifen Citrate, Temozolomide, Temsirolimus, Thalidomide, Topotecan Hydrochloride, Toremifene, Tositumomab and I 131 Iodine Tositumomab, Trastuzumab, Vincristine Sulfate, Vorinostat, and Zoledronic Acid.

16. A method for the treatment of prostate cancer, wherein an effective amount of a compound according to claim 1 is administered to a subject in need of such treatment.

17. A method for the treatment of prostate cancer, wherein an effective amount of a compound according to claim 8 is administered to a subject in need of such treatment.

\* \* \* \* \*